US010407731B2

(12) United States Patent
Klee et al.

(10) Patent No.: US 10,407,731 B2
(45) Date of Patent: Sep. 10, 2019

(54) BIOMARKER PANELS FOR PREDICTING PROSTATE CANCER OUTCOMES

(71) Applicant: MAYO FOUNDATION FOR MEDICAL EDUCATION AND RESEARCH, Rochester, MN (US)

(72) Inventors: George G. Klee, Rochester, MN (US); Robert B. Jenkins, Rochester, MN (US); Thomas M. Kollmeyer, Rochester, MN (US); Karla V. Ballman, Northfield, MN (US); Eric J. Bergstralh, Mazeppa, MN (US); Bruce W. Morlan, Northfield, MN (US); S. Keith Anderson, Rochester, MN (US); Tohru Nakagawa, Tokyo (JP)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 550 days.

(21) Appl. No.: 14/857,658

(22) Filed: Sep. 17, 2015

(65) Prior Publication Data
US 2016/0010162 A1 Jan. 14, 2016
US 2018/0312926 A9 Nov. 1, 2018

Related U.S. Application Data

(63) Continuation of application No. 12/474,879, filed on May 29, 2009, now abandoned.

(60) Provisional application No. 61/057,698, filed on May 30, 2008.

(51) Int. Cl.
*C12Q 1/6886* (2018.01)
*G16H 50/30* (2018.01)
*G16H 50/20* (2018.01)
*G16H 20/10* (2018.01)
*G06F 19/00* (2018.01)

(52) U.S. Cl.
CPC ........... *C12Q 1/6886* (2013.01); *G06F 19/00* (2013.01); *G16H 20/10* (2018.01); *G16H 50/20* (2018.01); *G16H 50/30* (2018.01); *C12Q 2600/118* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 3,645,691 A | 2/1972 | Guenter et al. |
| 3,687,808 A | 8/1972 | Thomas, Jr. et al. |
| 5,130,238 A | 7/1992 | Malek et al. |
| 5,143,854 A | 9/1992 | Pirrung et al. |
| 5,288,514 A | 2/1994 | Ellman |
| 5,384,261 A | 1/1995 | Winkle et al. |
| 5,399,491 A | 3/1995 | Kacian et al. |
| 5,455,166 A | 10/1995 | Walker |
| 5,494,810 A | 2/1996 | Barany et al. |
| 5,538,848 A | 7/1996 | Livak et al. |
| 5,677,195 A | 10/1997 | Winkler et al. |
| 5,705,365 A | 1/1998 | Ryder et al. |
| 5,710,029 A | 1/1998 | Ryder et al. |
| 5,744,305 A | 4/1998 | Fodor et al. |
| 5,830,711 A | 11/1998 | Barany et al. |
| 5,846,717 A | 12/1998 | Brow et al. |
| 5,854,033 A | 12/1998 | Lizardi |
| 5,888,779 A | 3/1999 | Kacian et al. |
| 5,965,360 A | 10/1999 | Zain et al. |
| 5,985,557 A | 11/1999 | Prudent et al. |
| 5,989,815 A | 11/1999 | Skolnick et al. |
| 5,994,069 A | 11/1999 | Hall et al. |
| 6,001,567 A | 12/1999 | Brow et al. |
| 6,022,692 A | 2/2000 | Coulie et al. |
| 6,027,887 A | 2/2000 | Zavada et al. |
| 6,090,543 A | 7/2000 | Prudent et al. |
| 6,136,182 A | 10/2000 | Dolan et al. |
| 6,218,523 B1 | 4/2001 | French |
| 6,225,051 B1 | 5/2001 | Sugiyama et al. |
| 6,251,639 B1 | 6/2001 | Kurn |
| 6,268,142 B1 | 7/2001 | Duff et al. |
| 6,410,278 B1 | 6/2002 | Notomi et al. |
| 6,436,642 B1 | 8/2002 | Gould-Rothberg et al. |
| 6,630,358 B1 | 10/2003 | Wagner et al. |
| 6,723,506 B2 | 4/2004 | Fletcher et al. |
| 7,186,514 B2 | 3/2007 | Zavada et al. |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,280,922 B2 | 10/2007 | Mei et al. |
| 7,300,788 B2 | 11/2007 | Matsuzaki et al. |
| 7,319,011 B2 | 1/2008 | Riggins et al. |
| 7,323,305 B2 | 1/2008 | Leamon et al. |
| 7,335,762 B2 | 2/2008 | Rothberg et al. |
| 7,358,061 B2 | 4/2008 | Yamamoto et al. |
| 7,361,488 B2 | 4/2008 | Fan et al. |
| 7,378,233 B2 | 5/2008 | Sidransky et al. |
| 7,407,755 B2 | 8/2008 | Lubinski et al. |
| 7,541,169 B2 | 6/2009 | Freimuth et al. |
| 7,598,052 B2 | 10/2009 | Giordanos et al. |

(Continued)

FOREIGN PATENT DOCUMENTS

EP 2 366 800 A1 9/2011
WO WO 1990/015070 A1 12/1990
(Continued)

OTHER PUBLICATIONS

US 5,962,233 A, 10/1999, Livak et al. (withdrawn)
(Continued)

Primary Examiner — Angela M. Bertagna
(74) Attorney, Agent, or Firm — Knobbe, Martens, Olson and Bear, LLP

(57) ABSTRACT

This document provides methods and materials related to assessing male mammals (e.g., humans) with prostate cancer. For example, methods and materials for predicting (1) which patients, at the time of PSA reoccurrence, will later develop systemic disease, (2) which patients, at the time of retropubic radial prostatectomy, will later develop systemic disease, and (3) which patients, at the time of systemic disease, will later die from prostate cancer are provided.

11 Claims, 8 Drawing Sheets

Specification includes a Sequence Listing.

(56) References Cited

U.S. PATENT DOCUMENTS

| | | |
|---|---|---|
| 7,662,553 B2 | 2/2010 | Lenz et al. |
| 7,767,391 B2 | 8/2010 | Scott et al. |
| 7,901,881 B2 | 3/2011 | Libutti et al. |
| 7,901,888 B2 | 3/2011 | Kebebew |
| 7,914,988 B1 | 3/2011 | Chudin et al. |
| 7,927,826 B2 | 4/2011 | Riggins et al. |
| 8,008,009 B2 | 8/2011 | Choquet-Kastylevsky et al. |
| 8,202,692 B2 | 6/2012 | Giordano et al. |
| 8,273,539 B2 | 9/2012 | Klee et al. |
| 8,293,880 B2 | 10/2012 | Cote et al. |
| 8,299,233 B2 | 10/2012 | Andre et al. |
| 8,338,109 B2 | 12/2012 | Vasmatzis et al. |
| 8,354,228 B2 | 1/2013 | Ron |
| 8,465,914 B2 | 6/2013 | Brown et al. |
| 8,541,170 B2 | 9/2013 | Kennedy et al. |
| 8,568,971 B2 | 10/2013 | Brown et al. |
| 8,669,057 B2 | 3/2014 | Kennedy et al. |
| 8,802,599 B2 | 8/2014 | Aharonov et al. |
| 8,828,656 B2 | 9/2014 | Bullerdiek et al. |
| 8,877,445 B2 | 11/2014 | Shackney |
| 8,945,829 B2 | 2/2015 | Keutgen et al. |
| 9,040,286 B2 | 5/2015 | Zon et al. |
| 9,074,258 B2 | 7/2015 | Davicion et al. |
| 9,096,906 B2 | 8/2015 | Aharonov et al. |
| 9,157,123 B2 | 10/2015 | Xing |
| 9,175,352 B2 | 11/2015 | Keutgen et al. |
| 9,206,482 B2 | 12/2015 | Davicioni et al. |
| 9,234,244 B2 | 1/2016 | Zeiger et al. |
| 9,495,515 B1 | 11/2016 | Giulia et al. |
| 9,587,279 B2 | 3/2017 | Fahey, III et al. |
| 9,617,604 B2 | 4/2017 | Davicion et al. |
| 9,708,667 B2 | 7/2017 | Yanai et al. |
| 9,714,452 B2 | 7/2017 | Davicioni et al. |
| 9,856,537 B2 | 1/2018 | Kennedy et al. |
| 9,994,907 B2 | 6/2018 | Davicioni et al. |
| 10,114,924 B2 | 10/2018 | Kennedy et al. |
| 2001/0051344 A1 | 12/2001 | Shalon et al. |
| 2002/0076735 A1 | 6/2002 | Williamset al. |
| 2002/0119463 A1 | 8/2002 | Fads |
| 2002/0168638 A1 | 11/2002 | Schlegel et al. |
| 2002/0169137 A1 | 11/2002 | Reineret al. |
| 2002/0182586 A1 | 12/2002 | Morris et al. |
| 2003/0119168 A1 | 6/2003 | Madison et al. |
| 2003/0152980 A1 | 8/2003 | Golub et al. |
| 2003/0186248 A1 | 10/2003 | Erlander et al. |
| 2003/0190602 A1 | 10/2003 | Pressman et al. |
| 2003/0194734 A1 | 10/2003 | Jatkoe |
| 2003/0224399 A1 | 12/2003 | Reed et al. |
| 2003/0235820 A1 | 12/2003 | Mack |
| 2004/0009481 A1 | 1/2004 | Schlegel et al. |
| 2004/0018493 A1 | 1/2004 | Anastasio et al. |
| 2004/0019466 A1 | 1/2004 | Minor et al. |
| 2004/0029114 A1 | 2/2004 | Mack et al. |
| 2004/0058378 A1 | 3/2004 | Kong et al. |
| 2004/0259086 A1 | 12/2004 | Schlegel et al. |
| 2005/0042222 A1 | 2/2005 | Yamamoto et al. |
| 2005/0048533 A1 | 3/2005 | Sidransky et al. |
| 2005/0064455 A1 | 3/2005 | Baker et al. |
| 2005/0118625 A1 | 6/2005 | Mounts |
| 2005/0137805 A1 | 6/2005 | Lewin et al. |
| 2005/0202442 A1 | 9/2005 | Morris et al. |
| 2005/0227917 A1 | 10/2005 | Williams et al. |
| 2005/0240357 A1 | 10/2005 | Minor |
| 2005/0250125 A1 | 11/2005 | Novakoff |
| 2005/0260646 A1 | 11/2005 | Baker et al. |
| 2005/0266443 A1 | 12/2005 | Croce et al. |
| 2006/0019256 A1 | 1/2006 | Clarke et al. |
| 2006/0019615 A1 | 1/2006 | Ditmer |
| 2006/0035244 A1 | 2/2006 | Riggins et al. |
| 2006/0046253 A1 | 3/2006 | Nakao |
| 2006/0083744 A1 | 4/2006 | Chen et al. |
| 2006/0088851 A1 | 4/2006 | Erlander et al. |
| 2006/0094061 A1 | 5/2006 | Brys et al. |
| 2006/0105360 A1 | 5/2006 | Croce et al. |
| 2006/0127907 A1 | 6/2006 | Matsubara et al. |
| 2006/0134663 A1 | 6/2006 | Harkin et al. |
| 2006/0204989 A1 | 9/2006 | Kopreski |
| 2006/0211017 A1 | 9/2006 | Chinnaiyan et al. |
| 2007/0020657 A1 | 1/2007 | Grebe et al. |
| 2007/0031873 A1 | 2/2007 | Wang et al. |
| 2007/0037165 A1 | 2/2007 | Venter et al. |
| 2007/0037186 A1 | 2/2007 | Jiang et al. |
| 2007/0048738 A1 | 3/2007 | Donkena et al. |
| 2007/0065827 A1 | 3/2007 | Pauloski et al. |
| 2007/0065833 A1 | 3/2007 | Gupta |
| 2007/0083334 A1 | 4/2007 | Mintz et al. |
| 2007/0099197 A1 | 5/2007 | Afar et al. |
| 2007/0099209 A1 | 5/2007 | Clarke et al. |
| 2007/0105133 A1 | 5/2007 | Clarke et al. |
| 2007/0148667 A1 | 6/2007 | Williams et al. |
| 2007/0148687 A1 | 6/2007 | Bedingham et al. |
| 2007/0161004 A1 | 7/2007 | Brown et al. |
| 2007/0172841 A1 | 7/2007 | Wang |
| 2007/0172844 A1 | 7/2007 | Lancaster et al. |
| 2007/0212702 A1 | 9/2007 | Tomlins et al. |
| 2007/0220621 A1 | 9/2007 | Clarke et al. |
| 2007/0238119 A1 | 10/2007 | Yu et al. |
| 2007/0259352 A1 | 11/2007 | Bentwich et al. |
| 2007/0275915 A1 | 11/2007 | Hallenbeck et al. |
| 2008/0009001 A1 | 1/2008 | Bettuzzi et al. |
| 2008/0028302 A1 | 1/2008 | Meschkat |
| 2008/0044824 A1 | 2/2008 | Giordano et al. |
| 2008/0076674 A1 | 3/2008 | Litman et al. |
| 2008/0124344 A1 | 5/2008 | Combs et al. |
| 2008/0131892 A1 | 6/2008 | Becker et al. |
| 2008/0145841 A1 | 6/2008 | Libutti et al. |
| 2008/0254470 A1 | 10/2008 | Berlkin |
| 2008/0274457 A1 | 11/2008 | Eng et al. |
| 2008/0281568 A1 | 11/2008 | Kao et al. |
| 2009/0020433 A1 | 1/2009 | Cohen et al. |
| 2009/0036415 A1 | 2/2009 | Rubin et al. |
| 2009/0062144 A1 | 3/2009 | Guo |
| 2009/0075921 A1 | 3/2009 | Ikegawa |
| 2009/0149333 A1 | 6/2009 | Knudsen et al. |
| 2009/0191535 A1 | 7/2009 | Connelly et al. |
| 2009/0204333 A1 | 8/2009 | Friend et al. |
| 2009/0239221 A1 | 9/2009 | Chinnaiyan et al. |
| 2009/0280490 A1 | 11/2009 | Baker et al. |
| 2009/0298082 A1 | 12/2009 | Klee et al. |
| 2010/0055704 A1 | 3/2010 | Giordano et al. |
| 2010/0075384 A1 | 3/2010 | Kong et al. |
| 2010/0099093 A1 | 4/2010 | Weaver et al. |
| 2010/0130377 A1 | 5/2010 | Vasmatzis et al. |
| 2010/0131286 A1 | 5/2010 | Houlgatte et al. |
| 2010/0131432 A1 | 5/2010 | Kennedyet al. |
| 2010/0178653 A1 | 7/2010 | Aharonov et al. |
| 2010/0257617 A1 | 10/2010 | Ami et al. |
| 2010/0279327 A1 | 11/2010 | Ossovskaya |
| 2010/0285979 A1 | 11/2010 | Zeiger et al. |
| 2011/0009286 A1 | 1/2011 | Andre et al. |
| 2011/0045462 A1 | 2/2011 | Fu et al. |
| 2011/0092375 A1 | 4/2011 | Zamore et al. |
| 2011/0136683 A1 | 6/2011 | Davicioni |
| 2011/0152110 A1 | 6/2011 | Vierlinger et al. |
| 2011/0178163 A1 | 7/2011 | Chowdhury |
| 2011/0212855 A1 | 9/2011 | Rafnar et al. |
| 2011/0229894 A1 | 9/2011 | Levy et al. |
| 2011/0230372 A1 | 9/2011 | Willman et al. |
| 2011/0236903 A1 | 9/2011 | McClelland |
| 2011/0287946 A1 | 11/2011 | Gudmundsson et al. |
| 2011/0294123 A1 | 12/2011 | Nakamura et al. |
| 2011/0312520 A1 | 12/2011 | Kennedy et al. |
| 2012/0015839 A1 | 1/2012 | Chinnaiyan |
| 2012/0015843 A1 | 1/2012 | Von et al. |
| 2012/0115743 A1 | 5/2012 | Davicioni et al. |
| 2012/0122698 A1 | 5/2012 | Stacey et al. |
| 2012/0122718 A1 | 5/2012 | Reisman |
| 2012/0157334 A1 | 6/2012 | Beaudenon-Huibregtse et al. |
| 2012/0172243 A1 | 7/2012 | Davicioni et al. |
| 2012/0214165 A1 | 8/2012 | Walfish et al. |
| 2012/0220474 A1 | 8/2012 | Kennedy et al. |
| 2012/0304318 A1 | 11/2012 | Ohnuma et al. |
| 2013/0004974 A1 | 1/2013 | Klee et al. |
| 2013/0023434 A1 | 1/2013 | Van Laar |

(56) References Cited

U.S. PATENT DOCUMENTS

| | | |
|---|---|---|
| 2013/0142728 A1 | 6/2013 | Beaudenon-Huibregtse et al. |
| 2013/0150257 A1 | 6/2013 | Abdueva et al. |
| 2013/0172203 A1 | 7/2013 | Yeatman et al. |
| 2013/0184999 A1 | 7/2013 | Ding |
| 2013/0225662 A1 | 8/2013 | Kennedy et al. |
| 2013/0231258 A1 | 9/2013 | Wilde et al. |
| 2013/0273543 A1 | 10/2013 | Gudmundsson et al. |
| 2013/0302808 A1 | 11/2013 | Vasmatzis |
| 2013/0302810 A1 | 11/2013 | Latham et al. |
| 2013/0303826 A1 | 11/2013 | Jurisica et al. |
| 2014/0066323 A1 | 3/2014 | Buerki et al. |
| 2014/0080731 A1 | 3/2014 | Davicioni et al. |
| 2014/0087961 A1 | 3/2014 | Sulem et al. |
| 2014/0099261 A1 | 4/2014 | Keutgen et al. |
| 2014/0121126 A1 | 5/2014 | Bivona et al. |
| 2014/0143188 A1 | 5/2014 | Mackey et al. |
| 2014/0228237 A1 | 8/2014 | Kennedy et al. |
| 2014/0243240 A1 | 8/2014 | Soldin et al. |
| 2014/0302042 A1 | 10/2014 | Chin et al. |
| 2014/0315199 A1 | 10/2014 | Rhodes et al. |
| 2014/0315739 A1 | 10/2014 | Aharonov et al. |
| 2014/0349856 A1 | 11/2014 | Schnabel et al. |
| 2014/0349864 A1 | 11/2014 | Kennedy et al. |
| 2014/0371096 A1 | 12/2014 | Umbright et al. |
| 2015/0011401 A1 | 1/2015 | Davicioni et al. |
| 2015/0038376 A1 | 2/2015 | Tian et al. |
| 2015/0099665 A1 | 4/2015 | Rosenfeld et al. |
| 2015/0141470 A1 | 5/2015 | Garraway et al. |
| 2015/0275306 A1 | 10/2015 | Bernards et al. |
| 2015/0299808 A1 | 10/2015 | Gonzalez et al. |
| 2015/0307947 A1 | 10/2015 | Basu et al. |
| 2015/0368724 A1 | 12/2015 | Aharonov et al. |
| 2016/0024586 A1 | 1/2016 | Delfour et al. |
| 2016/0032400 A1 | 2/2016 | Gomis et al. |
| 2016/0068915 A1 | 3/2016 | Kennedy et al. |
| 2016/0076108 A1 | 3/2016 | Davicioni et al. |
| 2016/0115546 A1 | 4/2016 | Rosenfeld et al. |
| 2016/0120832 A1 | 5/2016 | Rabinowitz et al. |
| 2016/0251729 A1 | 9/2016 | Chinnaiyan |
| 2016/0312305 A1 | 10/2016 | Kennedy et al. |
| 2016/0312306 A1 | 10/2016 | Kennedy et al. |
| 2016/0312307 A1 | 10/2016 | Kennedy et al. |
| 2016/0312308 A1 | 10/2016 | Kennedy et al. |
| 2016/0348184 A1 | 12/2016 | Chinnaiyan |
| 2017/0145513 A1 | 5/2017 | Kennedy et al. |
| 2017/0166980 A1 | 6/2017 | Fahey, III et al. |
| 2017/0329894 A1 | 11/2017 | Kennedy et al. |
| 2018/0016642 A1 | 1/2018 | Kennedy et al. |
| 2018/0030540 A1 | 2/2018 | Davicioni et al. |
| 2018/0068058 A1 | 3/2018 | Abdueva et al. |
| 2018/0122508 A1 | 5/2018 | Wilde et al. |
| 2018/0127832 A1 | 5/2018 | Kennedy et al. |

FOREIGN PATENT DOCUMENTS

| | | |
|---|---|---|
| WO | WO 1992/010092 A1 | 6/1992 |
| WO | WO 1993/009668 A1 | 5/1993 |
| WO | WO 1993/022684 A1 | 11/1993 |
| WO | WO 1998/045420 A2 | 10/1998 |
| WO | WO 2001/060860 A2 | 8/2001 |
| WO | WO 2001/066753 A1 | 9/2001 |
| WO | WO 20021000929 | 1/2002 |
| WO | WO 20031012067 | 2/2003 |
| WO | WO 2004/037972 A2 | 5/2004 |
| WO | WO 2005/040396 A2 | 5/2005 |
| WO | WO 2005/085471 A2 | 9/2005 |
| WO | WO 2005/100608 A2 | 10/2005 |
| WO | WO 2006/047484 A2 | 5/2006 |
| WO | WO 2006/091776 A2 | 8/2006 |
| WO | WO 2006/110264 A2 | 10/2006 |
| WO | WO 2006/127537 A2 | 11/2006 |
| WO | WO 2006/135596 | 12/2006 |
| WO | WO 2007/056049 | 5/2007 |
| WO | WO 2007/070621 | 6/2007 |
| WO | WO 2007/081720 A2 | 7/2007 |
| WO | WO 2008/023087 A2 | 2/2008 |
| WO | WO 2008/046911 A2 | 4/2008 |
| WO | WO 2008/086478 A2 | 7/2008 |
| WO | WO 2008/112283 A2 | 9/2008 |
| WO | WO 2009/009432 A2 | 1/2009 |
| WO | WO 2009/020521 A2 | 2/2009 |
| WO | WO 2009/020905 A2 | 2/2009 |
| WO | WO 2009/045115 | 4/2009 |
| WO | WO 2009/143603 A1 | 12/2009 |
| WO | WO 2010/056374 A2 | 5/2010 |
| WO | WO 2010/056374 A3 | 9/2010 |
| WO | WO 2010/099598 A1 | 9/2010 |
| WO | WO 2010/124372 A1 | 11/2010 |
| WO | WO 2011/150453 A1 | 12/2011 |
| WO | WO 2012/031008 A2 | 3/2012 |
| WO | WO 2012/068383 A2 | 5/2012 |
| WO | WO 2012/135008 A1 | 10/2012 |
| WO | WO 2013/088457 A1 | 6/2013 |
| WO | WO 2013/090620 A1 | 6/2013 |
| WO | WO 2014/028884 A2 | 2/2014 |
| WO | WO 2014/043803 A1 | 3/2014 |
| WO | WO 2015/071876 A2 | 5/2015 |
| WO | WO 2017/059549 A1 | 4/2017 |
| WO | WO 2018/165600 A1 | 9/2018 |

OTHER PUBLICATIONS

Robinson, M.D. & Speed, T.P. BMC Bioinformatics 2007; 8: 449 (Year: 2007).*
Probeset Listing for the Affymetrix Human Genome U133 Plus 2.0 array (Accessed from https://www.affymetrix.com/analysis/index.affx on Jul. 1, 2015) (Year: 2015).*
Nakagawa et al. PLoS ONE 2008; 3: e2318 (Year: 2008).*
Varambally et al. Cancer Cell 2005; 8: 393-406 (Year: 2005).*
Galamb et al. Cancer Epidemiology, Biomarkers & Prevention 2008; 17: 2835-2845 (Year: 2008).*
Rotunno et al. Cancer Prevention Research 2011; 4: 1-10 (Year: 2011).*
Liong et al. PLoS ONE 2012; 7: e45802 (Year: 2012).*
U.S. Appl. No. 61/057,698, filed May 30, 2008, Klee et al.
Alberts et al., Molecular Biology of the Cell, 3rd Ed., 1994, p. 465.
Authorized Officer Seate Giffo-Schmitt, International Preliminary Report on Patentability in PCT/US2007/079423 dated Apr. 9, 2009, 6 pages.
Authorized Officer Dorothee Mulhausen, International Preliminary Report on Patentability in PCT/US2007/83504 dated May 5, 2009, 4 pages.
Authorized Officer Kyu Jeong Ahn, International Search Report/Written Opinion in PCT/US2007/079423 dated Feb. 27, 2008, 10 pages.
Authorized Officer Kyu Jeong Ahn, International Search Report/Written Opinion in PCT/US2007/83504 dated Apr. 14, 2008, 3 pages.
Blute et al., "Use of Gleason score, prostate specific antigen, seminal vesicle and margin status to predict biochemical failure after radical prostatectomy," J Urol, 2001, 165: 119-125.
Bostwick et al., "Prognostic factors in prostate cancer: College of American Pathologists consensus statement," Arch Pathol Lab Med, 2000, 124(7):995-1000.
Epstein et al., "Prognostic factors and reporting of prostate carcinoma in radical AU prostatectomy and pelvic lymphadenectomy specimens," Scand. J. Urol. Nephrol. Suppl., 2005, 216:34-63.
Final Office Action for U.S. Appl. No. 12/442,685, 8 pages, dated Oct. 13, 2011.
Office Action for U.S. Appl. No. 12/442,685, 12 pages, dated May 24, 2011.
Gen Bank Accession No. AA462934 dated Jun. 10, 1997.
GenBank Accession No. AB028840 dated Jan. 12, 2000.
GenBank Accession No. AB030836 dated Oct. 23, 1999.
GenBank Accession No. AB0367 41 dated Dec. 22, 2000.
GenBank Accession No. AF077349 dated Dec. 14, 2000.
GenBank Accession No. AF077351 dated Dec. 20, 2000.
GenBank Accession No. AF115517 dated Nov. 23, 2005.
GenBank Accession No. AI413910 dated Feb. 9, 1999.

(56) References Cited

OTHER PUBLICATIONS

GenBank Accession No. AI414999 dated Feb. 9, 1999.
GenBank Accession No. AI425960 dated Mar. 9, 1999.
GenBank Accession No. AI851940 dated Jul. 15, 1999.
GenBank Accession No. AK018022 dated Sep. 19, 2008.
GenBank Accession No. AK019341 dated Sep. 19, 2008.
GenBank Accession No. AK019342 dated Sep. 19, 2008.
GenBank Accession No. AK142768 dated Sep. 19, 2008.
GenBank Accession No. AL591433 dated Jan. 15, 2009.
GenBank Accession No. BC004702 dated Jul. 15, 2006.
GenBank Accession No. BC055737 dated Jul. 15, 2006.
GenBank Accession No. BC086799 dated Sep. 21, 2006.
GenBank Accession No. BF449664 dated Dec. 1, 2000.
GenBank Accession No. BG063957 dated Jan. 26, 2001.
GenBank Accession No. BG077309 dated Dec. 17, 2003.
GenBank Accession No. BM114282 dated Jan. 30, 2002.
GenBank Accession No. BY023910 dated Dec. 6, 2002.
GenBank Accession No. CN724527 dated May 18, 2004.
Gen Bank Accession No. NM 000130 dated Oct. 18, 2009.
GenBank Accession No. NM 000493 dated Mar. 15, 2009.
GenBank Accession No. NM 001034 dated Oct. 5, 2009.
GenBank Accession No. NM 001049 dated Jun. 21, 2009.
GenBank Accession No. NM 001067 dated Oct. 18, 2009.
GenBank Accession No. NM_001136154 dated Jan. 8, 2012, 6 pages.
GenBank Accession No. NM_001136155 dated Jan. 8, 2012, 6 pages.
GenBank Accession No. NM 001786 dated Nov. 1, 2009.
GenBank Accession No. NM_001844 dated Aug. 28, 2009.
GenBank Accession No. NM_003873.3 dated Oct. 18, 2009.
GenBank Accession No. NM_004449 dated Jan. 8, 2012, 6 pages.
GenBank Accession No. NM_005025.2 dated Jul. 12, 2009.
GenBank Accession No. NM 005651.1 dated Oct. 27, 2009.
GenBank Accession No. NM 006558 dated 812109.
GenBank Accession No. NM_006727 dated Oct. 18, 2009.
GenBank Accession No. NM_018930 dated Feb. 10, 2008.
GenBank Accession No. NM_080607 dated Sep. 3, 2009.
GenBank Accession No. NM_133445 dated Sep. 20, 2009.
GenBank Accession No. NM_182918 dated Jan. 8, 2012, 6 pages.
Gen Bank Accession No. NP 001058 dated Dec. 25, 2011, 9 pages.
GenBank Accession No. W34764 dated May 13, 1996.
GenBank Accession No. NM_000598, GI No. 62243067, dated Jun. 6, 2010, 5 pages.
GenBank Accession No. NM_000688, GI No. 40316942, dated Apr. 11, 2010, 5 pages.
GenBank Accession No. NM001013398; GI No. 62243247, dated Jun. 6, 2010, 5 pages.
GenBank Accession No. NM001039573, GI No. 221316683, dated Mar. 4, 2010, 5 pages.
GenBank Accession No. NM_001098533, GI No. 237858579, dated May 7, 2010, 5 pages.
Gen Bank Accession No. NM_001130851; GI No. 195927024, dated Mar. 5, 2010, 4 pages.
GenBankAccession No. NM001143998, GI No. 221316675, dated Mar. 4, 2010, 5 pages.
GenBank Accession No. NM001143999, GI No. 221316679, dated Mar. 5, 2010, 5 pages.
Gen Bank Accession No. NM_001144001, GI No. 221316686, dated Mar. 4, 2010, 5 pages.
GenBank Accession No. NM001160367, GI No. 237858581, dated May 7, 2010, 5 pages.
GenBank Accession No. NM003003, GI No. 221316681, dated Mar. 4, 2010, 5 pages.
GenBank Accession No. NM_003014; GI No. 170784837, dated Mar. 13, 2010, 5 pages.
GenBank Accession No. NM_003184; GI No. 115527086, dated Mar. 7, 2010, 7 pages.
Gen Bank Accession No. NM004336; GI No. 211938448, dated Mar. 14, 2010, 6 pages.
GenBank Accession No. NM_005192, GI No. 195927023, dated Mar. 4, 2010, 4 pages.
GenBank Accession No. NM006265, GI No. 208879448, dated Apr. 11, 2010, 6 pages.
GenBank Accession No. NM006819; GI No. 110225356, dated May 7, 2010, 5 pages.
GenBank Accession No. NM012152; GI No. 183396778, dated Apr. 5, 2010, 5 pages.
GenBank Accession No. NM014846; GI No. 120952850, dated Mar. 4, 2010, 6 pages.
GenBank Accession No. NM_016623; GI No. 42734437, dated Mar. 29, 2009, 4 pages.
GenBank Accession No. NM_031966 GI No. 34304372, dated Jun. 6, 2010, 5 pages.
Gen Bank Accession No. NM_032334; GI No. 223468686, dated Mar. 5, 2010, 3 pages.
GenBank Accession No. NM_052987, GI No. 237858574, dated May 7, 2010, 5 pages.
GenBank Accession No. NM_052988, GI No. 237858573, dated May 7, 2010, 5 pages.
GenBankAccession No. NM_080546; GI No. 112363101, dated May 7, 2010, 6 pages.
GenBank Accession No. NM_ 138455; GI No. 34147546, dated May 7, 2010, 3 pages.
GenBank Accession No. NM_199166, GI No. 40316938, dated Apr. 11, 2010, 5 pages.
Amling et al.: "Long-term hazard of progression after radical prostatectomy for clinically EB localized prostate cancer continued risk of biochemical failure after 5 years," J Urol., 2000, 164:101-105.
Amundadottir et al.: "A common variant associated with prostate cancer in European and African populations," Nat Genet., 2006, 38:652-658.
Amundson et al.; "Integrating global gene expression and radiation survival parameters ED across the 60 cell lines of the National Cancer Institute Anticancer Drug Screen"; Cancer Research (2008) 68:415-424.
Ballman et al.: "Faster cyclic loess: normalizing RNA arrays via linear models," Bioinformatics, 2004, 20:2778-2786.
Bergstralh et al.; "Software for optimal matching in observational studies," Epidemiology, 1996, 7(3):331-332.
Best et al.: "Molecular differentiation of high- and moderate-grade human prostate cancer by cDNA microarray analysis,"; Diagn Mol Pathol., 2003, 12(2):63-70.
Bibikova et al.: "Expression signatures that correlated with Gleason score and relapse in 'prostate cancer,"; Genomics, 2007, 89(6):666-672.
Bibikova et al.: "Gene expression profiles in formalin-fixed, paraffin-embedded tissues obtained with a novel assay for microarray analysis," Clin Chem., 2004, 50:2384-2386.
Bibikova et al.: "Quantitative gene expression profiling in formalin-fixed, paraffinembedded tissues using universal bead arrays,"; Am J Pathol., 2004, 165:1799-1807.
Breiman: "Random Forests"; Machine Learning, 2001, 45:5-32.
Bull et al.: "Identification of potential diagnostic markers of prostate cancer and prostatic intraepithelial neoplasia using cDNA microarray"; Br J Cancer, 2001, 84(11 ):1512-1519.
Chen et al.; "Hepsin and maspin are inversely expressed in laser capture microdissectioned prostate cancer,"; J Ural., 2003, 169(4):1316-1319.
Cheville et al.: "Gene panel model predictive of outcome in men at high-risk of systemic orogression and death from prostate cancer after radical retropubic prostatectomy"; Journal lof Clinical Oncology (2008) 26, 3930-3936.
Colgne et al.: "Optimal Case-Control Matching in Practice" Epidemiology Resources Inc., 1995, 6(3):271-275.
D'Amico et al.: Cancer-specific mortality after surgery or radiation for patients with clinically localized prostate cancer managed during the prostate-specific antigen era 11 J Clin Oncol., 2003, 21:2163-2172.
D'Amico et al.: Determinants of prostate cancer-specific survival after radiation therapy for patients with clinically localized prostate cancer11 ; J Clin Oncol., 2002, 20:4567-4573.

(56) References Cited

OTHER PUBLICATIONS

De Marzo et al.: 11Pathological and molecular mechanisms of prostate carcinogenesis: implications for diagnosis, detection, prevention, and treatment"; J Cell Biochem., 2004, 91 (3):459-477.
Demichelis et al.: "TMPRSS2:ERG gene fusion associated with lethal prostate cancer in a watchful waiting cohort"; Oncogene, 2007, 26:4596-4599.
Dhanasekaran et al.: Delineation of prognostic biomarkers in prostate cancer11 ; Nature, 2001, 412:822-826.
Eder et al.: 11Genes differentially expressed in prostate cancer BJU Int., 2004, 93(8):1151-1155.
Ernst et al.,: Decrease and gain of gene expression are equally discriminatory markers for prostate carcinoma: a gene expression analysis on total and microdissected prostate tissue 11; Am J Pathol., 2002, 160(6):2169-2180.
Fan et al.:"Concordance among gene expression-based predictors for breast cancer"; N Engl J Med., 2006, 355:560-569.
Foley et al.: 11 Molecular pathology of prostate cancer: the key to identifying new biomarkers of disease 11 ; Endocrine-Related Cancer, 2004, 11 :477-488.
Gleason: 11 Histologic grading and clinical staging of prostatic carcinoma 11 ; Urologic pathology: the prostate, (Tannenbaum, ed., 1977) Lea & Febiger, Philadelphia, PA, pp. 171-197.
Gleason: "Histologic grading of prostate cancer: a perspective"; Hum. Pathol., 1992, 23(3):273-279.
Gleave et al.: "Randomized comparative study of 3 versus 8-month neoadjuvant hormonal therapy before radical prostatectomy: biochemical and pathological effects"; J Urol., 2001, 166:500-507.
Glinsky et al.: "Gene expression profiling predicts clinical outcome of prostate cancer"; J Clin Invest., 2004, 113:913-923.
Glinsky et al.: "Microarray analysis identifies a death-from-cancer signature predicting therapy i failure in patients with multiple types of cancer"; J Clin Invest., 2005, 115: 1503-1521.
Gonzalgo et al: "Molecular pathways to prostate cancer"; J Urol., 2003, 170(6 Pt 1):2444-2452.
Greenbaum et al.: "Comparing protein abundance and mRNA expression levels on a ~enomic scale";Genome Biology, 2003, 4(9):117.1-117.8.
Greenbaum et al.: "Comparing protein abundance and mRNA expression levels on a genomic scale"; Genome Biology, 2003, 4(9):117.1-117.8.
Haiman et al.: "Multiple regions within 8q24 independently affect risk for prostate cancer"; Nat Genet., 2007, 39:638-644.
Henrotin et al.: "Type II collagen peptides for measuring cartilage degradation"; Biotheology, 2004, 41 (3-4):Abstract.
Holzbeierlein et al.: "Gene expression analysis of human prostate carcinoma during hormonal therapy identifies androgen-responsive genes and mechanisms of therapy resistance"; American Journal of Pathology (2004) 164(1), 217 227.
Hughes et al.: "Molecular pathology of prostate cancer"; J Clin Pathol., 2005, 58(7):673-~84.
Humphrey et al: "Histologic grade, DNA ploidy, and intraglandular tumor extent as indicators of tumor progression of clinical Stage B prostatic carcinoma"; Am J Surg Pathol, 1991, 15(12):1165-1170.
Jemal et al.: "Cancer statistics"; CA Cancer J Clin., 2005, 55:10-30.
Karan et al.: "Current status of the molecular genetics of human prostatic adenocarcinomas"; Int J Cancer, 2003, 103(3):285-293.
Kara Yi et al: Molecular biology of prostate cancer; Prostate Cancer Prostatic Dis., 2004, 7(1 ):6-20.
Kestin: "Potential survival advantage with early androgen deprivation for biochemical failure after external beam radiotherapy: the importance of accurately defining biochemical disease status"; Int J Rad Oneal Biol Phis., 2004, 60:453-62.
Kosar! et al.: "Identification of biomarkers for prostate cancer"; Clin. Cancer Res., 2008, 1734-1743.
Kube et al.: "Optimization of laser capture microdissection and RNA amplification for gene expression profiling of prostate cancer"; BMC Mol. Biol., 2007, 8:25.

Lapointe et al.: "Gene expression profiling identifies clinically relevant subtypes of prostate cancer"; Proc Natl Acad Sci USA, 2004, 101 :811-816.
Latulippe et al.: "Comprehensive Gene Expression Analysis of Prostate Cancer Reveals Distinct Transcriptional Programs Associated with Metastatic Disease"; Cancer Res., 2002, 62:4499-4506.
Lawton et al.: "Updated results of the phase III Radiation Therapy Oncology Group (RTOG) trial 85-31 evaluating the potential benefit of androgen suppression following standard radiation therapy for unfavorable prognosis carcinoma of the prostate"; Int J Rad Oneal Biol Phis 2001, 49:937-946.
Luo et al.: "Gene expression analysis of prostate cancers"; Mol Carcinog., 2002, 33(1 ):25-35.
Luo et al.: "Human Prostate Cancer and Benign Prostatic Hyperplasia: Molecular Dissection by Gene Expression Profiling"; Cancer Res., 2001, 61 :4683-4688.
Maggee al.: "Expression Profiling Reveals Hepsin Overexpression in Prostate Cancer"; Cancer Res., 2001, 61:5692-5696.
Montironi et al.; "Carcinoma of the prostate: inherited susceptibility, somatic gene defects and androgen receptors", Virchows Arch., 2004, 444(6):503-508.
Moul et al.: "Early versus delayed hormonal therapy for prostate specific antigen only recurrence of prostate cancer after radical prostatectomy"; J Ural., 2004, 171 :1141-1147.
Moul et al.: "Prostate specific antigen only progression of prostate cancer"; J Urol., 2000, 163:1632-42.
Nakagawa et al.: "A tissue biomarker panel predicting systemic progression after PSA recurrence post-definitie prostate cancer therapy"; PLOS one, 2008, 3(5): e2318, pp. 1-13.
Ohl et al.: "Gene expression studies in prostate cancer tissue: which reference gene should be selected for normalization?"; J. Mol. Med., 2005, 83:1014-1024.
Parker et al.: "High expression levels of survivin protein independently predict a poor GD outcome for patients who undergo surgery for clear cell renal cell carcinoma"; Cancer, Q006, 107:37-45.
Pascal et al.: "Correlation of mRNA and protein levels: cell type-specific gene expression of cluster designation antigens in the prostate"; BMC Genomics (2008) 9: 246 (13 pages).
Pa Tel et al.: "Preoperative PSA velocity is a independent prognostic factor for relapse after radical prostatectomy"; J Clin Oncol., 2005, 23:6157-6162.
Pienta et al. "The current state of preclinical prostate cancer animal models"; Prostate (2008) 69: 629-639.
Pilepich et al.: "Phase III radiation therapy oncology group (RTOG) trial 86-10 of androgen deprivation adjuvant to definitive radiotherapy in locally advanced carcinoma of the prostate"; IntJ Rad Oncol Biol Phis., 2001, 50:1243-1252.
Pinover et al.: "Validation of a treatment policy for patients with prostate specific antigen failure after three-dimensional conformal prostate radiation therapy"; Cancer, 2003, 97:1127-1133.
Porkka et al: Molecular mechanisms of prostate cancer; Eur Urol., 2004, 45(6):683-691.
Porkka et al: "Natural history of progression after PSA elevation following radical prostatectomy"; JAMA, 1999, 281:1591-1597.
Rhodes et al.: "Large-scale meta-analysis of cancer microarray data identifies common transcriptional profiles of neoplastic transformation and progression"; Proc Natl Acad Sci USA,. 2004, 101 :9309-9314.
Rhodes et al.: "ONCOMINE: A Cancer Microarray Database and Integrated Data-Mining Platform"; Neoplasia, 2004, 6:1-6.
Robertson et al.: "DNA in radical prostatectomy specimens. Prognostic value of tumor iploidy"; Acta Oncol, 1991, 30(2):205-207.
Rubin et al.: "Molecular genetics of human prostate cancer"; Mod Pathol., 2004, 17(3):380-388.
Sandler et al.: "Overall survival after prostate-specific-antigen-detected recurrence following conformal radiation therapy"; Int J Rad Oneal Biol Phis., 2000, 48:629-633.
Saramaki et al.: "Amplification of EIF3S3 gene is associated with advanced stage in !prostate cancer"; Am J Pathol., 2001, 159:2089-2094.
Savinainen et al.: "Expression and copy number analysis of TRPS 1, EIF3S3 and MYC genes in breast and prostate cancer"; Br J Cancer, 2004, 90:1041-1046.

(56) References Cited

OTHER PUBLICATIONS

Savinainen et al.: "Over expression of EIF3S3 promotes cancer cell growth"; Prostate, 12006, 66:1144-1150.
Schumacher et al.: "A Common 8q24 Variant in Prostate and Breast Cancer from a Large Nested Case-Control Study"; Cancer Res., 2007, 67:2951-2956.
Severi et al.: "The common variant rs1447295 on chromosome 8q24 and prostate cancer risk: results from an Australian population based case-control study"; Cancer Epidemiol, Biomarkers Prey., 2007, 16:610-611.
Shipley et al.: "Radiation therapy for clinically localized prostate cancer: a multiinstitutional pooled analysis"; JAMA, 1999, 281: 1598-1604.
Singh et al.: "Gene expression correlates of clinical prostate cancer behavior"; Cancer Cell, 2002, 1 :203-209.
Stamey et al.: "Molecular genetic profiling of Gleason grade 415 prostate cancers compared to benign prostatichyperplasia"; J Urol., 2001, 166(6):2171-2177.
Stephenson et al.: "Integration of gene expression profiling and clinical variables to predict prostate carcinoma recurrence after radical prostatectomy"; Cancer (2005) 104(2):290-298.
Subramanian et al.: "Gene set enrichment analysis: A knowledge-based approach for interpreting genome-wide expression profiles"; Proc Natl Acad Sci USA, 2005, 102(43):15545-15550.
Supplemental Table 1 of U.S. Appl. No. 61/057,698, filed May 30, 2008, 13 pages.
Supplemental Table 2 of U.S. Appl. No. 61/057,698, filed May 30, 2008, 15 pages.
Supplemental Table 3 of U.S. Appl. No. 61/057,698, filed May 30, 2008, 21 pages.
Supplemental Table 4 of U.S. Appl. No. 61/057,698, filed May 30, 12008, 1 page.
Supplemental Table 5 of U.S. Appl. No. 61/057,698, filed May 30, 12008, 2 pages.
Supplemental Table 6 of U.S. Appl. No. 61/057,698, filed May 30, 2008, 1 page.
Tockman et al.: "Considerations in bringing a cancer biomarker to clinical application"; Cancer Research, 1992, 52:2711 s-2718s.
Tollefson et al.: "Stratification of Patient Risk Based on Prostate-Specific Antigen Doubling Time After Radical Retropubic Prostatectomy"; Mayo Clin Proc., 2007, 82:422-427.
Tomlins et al.: "Integrative molecular concept modeling of prostate cancer progression"; Nat Genet., 2007, 39:41-51.
Tomlins et al.: "Recurrent Fusion of TMPRSS2 and ETS Transcription Factor Genes in Prostate Cancer"; Science, 2005, 310(5748):644-648.
Tomlins et al.: TMPRSS2:ETV4 Gene Fusions Define a Third Molecular Subtype of Prostate Res., 2006, 66:3396-3400.
Tricoli et al.: "Detection of prostate cancer and predicting progression: current and future diagnostic markers"; Clinical Cancer Research 2004, 10:3943-3953.
Tsuchiya et al.: "Clinical significance in situ hybridization analysis in pathologic of alterations of chromosome 8 detected by fluorescence organ-confined prostate cancer"; Genes Chromosomes Cancer, 2002, 34:363-371.
Tsuchiya et al.: "Mapping and gene expression profile of the minimally overrepresented 8q24 region in prostate cancer"; Am J Pathol., 2002, 160:1799-1806.
Varamball Yet al.: "Integrative Genomic and Proteomic Analysis of Prostate Cancer Reveals Signatures of Metastatic Progression"; Cancer Cell, Nov. 8, 2005(5):393-406.
Visakorpi: "The molecular genetics of prostate cancer"; Urology, 2003, 62 Suppl 1: 19-35.
Wang et al.: "Two common chromosome 8q24 variants are associated with increased risk for prostate cancer"; Cancer Res., 2007, 67:2944-2950.
Watson et al: "Future opportunities for the diagnosis and treatment of prostate cancer"; Prostate Cancer Prostatic Dis., 2004, 7:S8-S13.

Welsh et al.: "Analysis of Gene Expression Identifies Candidate Markers and Pharmacological Targets in Prostate Cancer"; Cancer Res., 2001, 61 :5974-5978.
Winkler et al.: "Stage D1 prostatic adenocarcinoma: significance of nuclear DNA ploidy patterns studied by flow cytometry"; Mayo Clin Proc. 1988, 63(2): 103-112.
Yeager et al.: "Genome-wide association study of prostate cancer identifies a second risk locus at 8q24"; Nat Genet., 2007, 39:645-649.
Yu et al.: "Gene expression alterations in prostate cancer predicting tumor aggression and preceding development of malignancy"; J Clin Oneal., 2004, 22(14):2790-2799.
Zanett A et al.: "Flow-cytometric analysis of deoxyribonucleic acid content in advanced ovarian carcinoma: its importance in long-term survival"; Am J Obstet Gynecol, 1996, 175(5): 1217-1225.
Zelefsky et al.: "Neoadjuvant hormonal therapy improves the therapeutic ratio in patients with bulky prostatic cancer treated with three-dimensional conformal radiation therapy"; Int J Radiat Oncol Biol Phys., 1994, 29:755-761.
Abdueva et al., "Quantitative Expression Profiting in Formalin-Fixed Paraffin-Embedded Samples by Affymetrix Microarrays," Journal of Molecular Diagnostics, vol. 12, No. 4, Jul. 2010, pp. 4 O 9 - 417.
Agell et al., "A 12-Gene Expression Signature is Associated with Aggressive Histological in Prostate Cancer: SEC14L1 and TCEB1 Genes Are Potential Markers of Progression," Am J Pathol, 2012, vol. 181 (5), pp. 1585-1594.
Aldred et al., "Papillary and follicular thyroid carcinomas show distinctly different microarray expression profiles and can be distinguished by a minimum of five genes," J Clin Oncol. (2004) 22(17):3531-9.
Ausubel, et al. Current Protocols in Molecular Biology. Wiley & Sons, New York, 1995, Table of Contents.
Baetke et al., "Molecular Pathways Involved in Prostate Carcinogenesis: Insights from Public Microarray Datasets," PLoS One (2012), 7(11):e49831, 1-11.
Bannert et al., "Retroelements and the human genome: new perspectives on an old relation." PNAS (Oct. 5, 2004) vol. 101, Suppl. 2, pp. 14572-14579.
Bauer et al., "Identification of Markers of Taxane Sensitivity Using Proteomic and Genomic Analyses of Breast Tumor from Patients Receiving Neoadjuvant Paclitaxel and Radiation," Clin. Cancer Res. (2010), 16(2):681-690, American Association for Cancer Research.
Birney et al., "Identification and analysis of functional elements in 1% of the human genome by the ENCODE pilot project." Nature. 2007 Jun. 14; 447(7146):799-816.
Boorjian et al., "Long-term risk of clinical progression after biochemical recurrence following radical prostatectomy: the impact of time from surgery to recurrence." Eur Urol. Jun. 2011; 59(6):893-9.
Boormans et al., "Identification of TDRD1 as a direct target gene of ERG in primary prostate cancer," Int J Cancer, (2013) vol. 133 (2), pp. 335-345.
Bott et al., "Prostate cancer management: (2) an update on locally advanced and metastatic disease", Postgrad Med J, Dec. 3 2003, 79(937), 643-645.
Brouha et al., "Hot L1s account for the bulk of retrotransposition in the human population." Proc Natl Acad Sci U S A. Apr. 29, 2003; 100(9):5280-5.
Bussmakers et al., "DD3: a new prostate-specific gene, highly overexpressed in prostate cancer." Cancer Res. Dec. 1, 1999; 59(23):5975-9.
Cerutti et al. "Diagnosis of suspicious thyroid nodules using four protein biomarkers," Clin Cancer Res. 2006;12(11 Pt 1):3311-8.
Chalitchagorn et al., "Distinctive pattern of LINE-1 methylation level in normal tissues and the association with carcinogenesis." Oncogene, Nov. 18, 2004; 23(54):8841-6.
Che et al.: "Prognostic Value of Abnormal p53 Expression in Locally Advanced Prostate Cancer Treated With Androgen Deprivation and Radiotherapy: A Study Based on RTOG 9202"; International Journal of Radiation: Oncology Biology Physics (Nov. 15, 2007) vol. 69, No. 4, pp. 1117-1123.

(56) References Cited

OTHER PUBLICATIONS

Chen et al.: "Molecular determinants of resistance to antiandrogen therapy"; Nature Medicine, Nature Publishing Group, New York, NY, vol. 10, No. 1, Jan. 1, 2004, pp. 33-39.
Chen et al., "Significance of noninvasive diagnosis of prostate cancer with cytologic examination of prostatic fluid," J Nippon Med Sch., 73(3):129-135, Jun. 2006.
Chen et al., "Deregulation of a Hox Protein Regulatory Network Spanning Prostate Cancer Initiation and Progression," Clin Cancer Res (Jun. 2012) 18(16):4291-4302.
Cheng et al. "Cell Proliferation in Prostate Cancer Patients with Lymph Node Metastasis", Clin Cancer Res, Oct. 1999, 5(10):2820-2823.
Chifman et al., "Conservation of immune gene signatures in solid tumors and prognostic implications," BMC Cancer (2016) 16:911, pp. 1-17. DOI 10.1186/S12885-016-2948-Z.
Chow et al., "LINE-1 activity in facultative heterochromatin formation during X chromosome inactivation." Cell. Jun. 11, 2010; 141(6):956-69.
Cibas, et al. "The Bethesda System for Reporting Thyroid Cytopathology," Am J Clin Pathol. (Nov. 2009) 132(5):658-65. doi: 10.1309/AJCPPHLWMI3JV4LA.
Clancy et al., "Profiling networks of distinct immune-cells in tumors," BMC Bioinformatics (2016) 17:263, pp. 1-15. DOI 10.1186/s12859-016-1141-3.
Clark-Langone et al. "Biomarker discovery for colon cancer using a 761 gene RT-PCR assay 2007," BMC Genomics 8:279 pp. 1-18 2007.
Cooperberg et al., "The CAPRA-S score: A straightforward tool for improved prediction of outcomes after radical prostatectomy," Cancer (2011) vol. 117 (22), pp. 5039-46.
Cordaux et al., "The impact of retrotransposons on human genome evolution." Nat Rev Genet. Oct. 2009; 10 10):691-703.
Cuzik et al., "Prognostic value of an RNA expression signature derived from cell cycle proliferation genes in patients with prostate cancer: a retrospective study," thelancet.com/oncology (Mar. 2011) vol. 12, pp. 245-255.
Dalela et al., "Contemporary Role of the Decipher Test in Prostate Cancer Management: Current Practice and Future Perspectives," Rev. Urol. (2016), 18(1):1-9, MedReviews®, LLC.
Dalsgaard Sorensen et al.: "Discovery of prostate cancer biomarkers by microarray gene expression profiling"; Expert Review of Molecular Diagnostics, vol. 10, No. 1, Jan. 1, 2010, pp.49-64.
Dawood, Shaheenah, "Novel Biomarkers of Metastatic Cancer," Expert Rev. Mo/. Diagn. (2010), 10(5):581-590, Expert Reviews Ltd.
Day et al., "Estimating enrichment of repetitive elements from high-throughput sequence data." Genome Biol. 2010; 11 6):R69.
Dechassa et al., "Architecture of the SWI/SNF-nucleosome complex," Mol Cell Biol. (Oct. 2008) vol. 28, No. 19, pp. 6010-6021.
Dougherty, "The fundamental role of pattern recognition for gene-expression/microarray data in bioinformatics," Pattern recognition. 2005; 38:2226-2228.
Edwards et al.: "MicroRNAs and Ultraconserved Genes as Diagnostic Markers and Therapeutic Targets in Cancer and Cardiovascular Diseases", Journal of Cardiovascular Translational Research, vol. 3, No. 3, May 5, 2010, pp. 271-279.
Englisch, et al., "Chemically Modified Oligonucleotides as Probes and Inhibitors," Angew. Chem. Int. Ed. Eng. 1991; 30:613-629.
Erho et al., "Discovery and Validation of a Prostate Cancer Genomic Classifier that Predicts Early Metastasis Following Radical Prostatectomy," PLoS ONE (2013), 8(6):e66855, 1-12.
Etzioni et al. "The case for early detection", Nature Reviews | Cancer, vol. 3, Apr. 2003, pp. 1-10.
Finley et al., "Discrimination of benign and malignant thyroid nodules by molecular profiling," Ann Surg. (2004) 240(3):425-36; discussion 436-7.
Finley et al., "Advancing the molecular diagnosis of thyroid nodules: defining benign lesions by molecular profiling," Thyroid (2005) 15(6):562-8.

Fodor et al., "Light-directed, spatially addressable parallel chemical synthesis," Science. Feb. 15, 1991; 251(4995):767-73.
Fontaine, et al., "Increasing the number of thyroid lesions classes in microarray analysis improves the relevance of diagnostic markers," PLoS One. Oct. 29, 2009; 4(10):e7632. doi: 10.1371/journal.pone.0007632.
Fryknas et al., "Molecular markers for discrimination of benign and malignant follicular thyroid tumors," Tumour Biol. (2006) 27(4):211-20.
Fujarewicz et al., "A multi-gene approach to differentiate papillary thyroid carcinoma from benign lesions: gene selection using support vector machines with bootstrapping," Endocr Relat Cancer (Sep. 2007) 14(3):809-26.
Gait. Chapter 16: Oligoribonucleotides. Antisense Research and Applications, Crookeand Lebleu Eds., CRC Press (pp. 289-302) (1993).
Gao et al., "VISTA is an inhibitory immune checkpoint that is increased after ipilimumab therapy in patients with prostate cancer," Nat Med. (May 2017) 23(5):551-555.
Genevieve de Saint Basile et al., "Severe Combined Immunodeficiency Caused by Deficiency in Either the Ii or the E Subunit of CD3," Journal of Clinical Investigation (2004) vol. 114, No. 10. p. 1512-1517.
Gibb et al., " The functional role of long non-coding RNA in human carcinomas", Molecular Cancer, Biomed Central, London, GB, vol. 10, No. 1, Apr. 13, 2011, p. 38.
Griffith et al., "Meta-analysis and meta-review of thyroid cancer gene expression profiling studies identifies important diagnostic biomarkers," J Clin Oncol. (2006) 24(31):5043-51.
Griffith, et al. Biomarker panel diagnosis of thyroid cancer: a critical review. Expert Rev Anticancer Ther. Sep. 2008;8(9):1399-413. doi: 10.1586/14737140.8.9.1399.
Gupta et al., "Long non-coding RNA HOTAIR reprograms chromatin state to promote cancer metastasis," Nature (Apr. 15, 2010) 464(7291): 1071-6.
Guttman et al., "Chromatin signature reveals over a thousand highly conserved large non-coding RNAs in mammals", Nature (Mar. 12, 2009) 458(7235):223-7.
Guttman et al., "Ab initio reconstruction of transcriptomes of pluripotent and lineage committed cells reveals gene structures of thousands of lincRNAs," Nat Biotechnol. (May 2010) 28(5):503-10.
Hamada et al., "Diagnostic usefulness of PCR profiling of the differentially expressed marker genes in thyroid papillary carcinomas," Cancer Lett. (Jun. 28, 2005) 224(2):289-301. Epub Nov. 18, 2004.
He et al., "The antisense transcriptomes of human cells", Science (Dec. 19, 2008) 322(5909): 1855-7.
Heemers, H. V. et al.: "Identification of a Clinically Relevant Androgen-Dependent Gene Signature in Prostate Cancer"; Cancer Research (2011) vol. 71, No. 5, pp. 1978- 1988.
Heidenreich et al., "EAU Guidelines on Prostate Cancer. Part 1: Screening, Diagnosis, and Treatment of Clinically Localised Disease," European Urology (2011) vol. 59, pp. 61-71.
Henshall et al., "Survival Analysis of Genome-Wide Gene Expression Profiles of Prostate ancers Identifies New Prognostic Targets of Disease Relapse," Cancer Research 63, 14196-4203, Jul. 15, 2003.
Hornberger et al., "A Multigene Prognostic Assay for Selection of Adjuvant Chemotherapy in Patients with T3, Stage II Colon Cancer: Impact on Quality-Adjusted Life Expectancy and Costs," Value in Health 15 (2012) pp. 1014-1021.
Huarte et al., "Large non-coding RNAs: missing links in cancer?" Human Molecular Genetics (Oct. 15, 2010) 19(2): R152- R161.
Hughes et al., "Topoisomerase II—a expression increases with increasing Gleason score and with hormone insensitivity in prostate carcinoma," J Clin Pathol. (Jul. 2006) 59(7): 721-724.
Jhavar et al., "Integration of ERG gene mapping and gene☐expression profiling identifies distinct categories of human prostate cancer," BJUI (2008) vol. 103 (9), pp. 1256-1269.
Kanehisa, "Use of statistical criteria for screening potential homologies in nucleic acid sequences," Nucleic Acids Res. (Jan. 11, 1984) 12(1 Pt 1):203-13.

(56) References Cited

OTHER PUBLICATIONS

Karnes et al., "The ability of biomarkers to predict systemic progression in men with high-risk prostate cancer treated surgically is dependent on ERG status," Cancer Res. (Nov. 9, 2010) 70(22):8994-9002, Epub.

Kasraeian, et al., "A comparison of fine-needle aspiration, core biopsy, and surgical biopsy in the diagnosis of extremity soft tissue masses," Clin Orthop Relat Res. (Nov. 2010) 468(11):2992-3002.

Kebebew et al., "Diagnostic and extent of disease multigene assay for malignant thyroid neoplasms," Cancer (2006) 106(12):2592-7.

Khor et al.: "Bcl-2 and Bax Expression Predict Prostate Cancer Outcome in Men Treated with Androgen Deprivation and Radiotherapy on Radiation Therapy Oncology Group Protocol 92-02"; Clinical Cancer Research (Jun. 15, 2007) vol. 13, No. 12, pp. 3585-3590.

Kiessling, et al., "D-TMPP: a novel androgen-regulated gene preferentially expressed in prostate and prostate cancer that is the first characterized member of an eukaryotic gene family," The Prostate (2005) 64:387-400.

Kikuchi et al., "Expression profiles of non-small cell lung cancers on cDNA microarrays: identification of genes for prediction of lymph-node metastasis and sensitivity to anti-cancer drugs," Oncogene (2003) 22, pp. 2192-2205.

Kishi et al., "Expression of the survivin gene in prostate cancer: correlation with clinicopathological characteristics, proliferative activity and apoptosis," J Urol. (May 2004) 171(5): 1855-1860.

Koshkin et al., "LNA (locked nucleic acids): an RNA mimic forming exceedingly stable LNA," LNA duplexes. J Am Chem Soc 120:13252-13253 (1998).

Koshkin et al., "LNA (locked nucleic acids): synthesis of the adenine, cytosine, guanine 5-methylcytosine, thymine and uracil bicyclonucleoside monomers, oligomerisation, and unprecedented nucleic acid recognition," Tetrahedron (1998) 54(14):3607-3630.

Kroschwitz The Concise Encyclopedia of Polymer Science and Engineering. (pp. 858-859) (1990).

Kumar, et al., "The first analogues of LNA (locked nucleic acids): phosphorothioate-LNA and 2'-thio-LNA," Bioorg Med Chem Lett. (Aug. 18, 1998) 8(16):2219-22

Landers et al.: "Use of multiple biomarkers for a molecular diagnosis of prostate cancer," Int. J. Cancer (May 10, 2005) 114 pp. 950-956.

Lin et al., "Nuclear receptor-induced chromosomal proximity and DNA breaks underlie specific translocations in cancer," Cell (Dec. 11, 2009) 139(6):1069-83.

Lockstone, "Exon array data analysis using Affymetrix power tools and R statistical software," Briefings in bioinformatics (2011) vol. 12 (6), pp. 634-644.

Martens-Uzunova, E. S. et al.: "Diagnostic and prognostic signatures from the small non-coding RNA transcriptome in prostate cancer", Oncogene (Jul. 18, 2011) vol. 31, No. 8, pp. 978-991.

Martin, "A New Access to 2'-O-Alkylated Ribonucleosides and Properties of 2'-O-Alkylated Oligoribonucleotides," Helv. Chim. Acta. (1995) 78:486-504. (in German with English abstract).

Mazzanti, et al., "Using gene expression profiling to differentiate benign versus malignant thyroid tumors," Cancer Res. (Apr. 15, 2004) 64(8):2898-903.

McCall et al., "Frozen robust multiarray analysis (fRMA)", Biostatistics (2010) vol. 11 (2), 242-253.

Mercer, DW, "Use of multiple markers to enhance clinical utility", Immunol Ser. (1990) 53: 39-54.

Mineva et al., "Differential expression of alphaB-crystallin and Hsp27-1 in anaplastic thyroid carcinomas because of tumor-specific alphaB-crystallin gene (CRYAB) silencing," Cell Stress Chaperones (2005) Autumn;10(3):171-84.

Newson, Roger, "Confidence intervals for rank statistics: Somers' D and extensions", Stata Journal (Sep. 2006) 6(3):309-334.

Nielsen et al., "Sequence-selective recognition of DNA by strand displacement with a thymine-substituted polyamide," (1991) Science. 254: 1497-1500.

Noordzij et al. "The prognostic value of CD44 isoforms in prostate cancer patients treated by radical prostatectomy", Clin Cancer Res (May 1997) 3(5): 805 -815.

Norman, James, "Thyroid Nodule Ultrasound", Endocrine website, Updated Oct. 13, 2010, http://www.endocrineweb.com/noduleus.html.

Penney et al., "mRNA Expression Signature of Gleason Grade Predicts Lethal Prostate Cancer," J Clin Oncol (Jun. 10, 2011) vol. 29, No. 17, pp. 2391-2396.

Penney et al., "Appendix (online only) of Penney et al., J Clin Oncol 29:2391 (Jun. 2011; online May 2, 2011)" pp. 1-9.

Perez et al., "Long, abundantly expressed non-coding transcripts are altered in cancer," Human Molecular Genetics (2008) vol. 17, No. 5, pp. 642-655. Published online Nov. 15, 2007.

Pittoni et al., "The Dark Side of Mast Cell-Targeted Therapy in Prostate Cancer," Cancer Res. (2012) 72(4):831-835.

Porkka et al., "RAD21 and KIAA0196 at 8q24 are amplified and overexpressed in prostate cancer," Genes Chromosomes Cancer (2007) 39:1-10.

Pound et al., "Natural history of progression after PSA elevation following radical prostatectomy," JAMA (1999) 281:1591-1597.

Prasad et al., "Identification of genes differentially expressed in benign versus malignant thyroid tumors," Clin Cancer Res. (2008) 14(11):3327-37.

Prensner et al., "Transcriptome Sequencing Identifies PCAT-1, a Novel lincRNA Implicated in Prostate Cancer Progression," (2012) 29 (8): 742-749.

Puskas, et al., "Gene profiling identifies genes specific for well-differentiated epithelial thyroid tumors," Cell Mol Biol (Noisy-le-grand) (Sep. 5, 2005) 51(2):177-86.

Reis et al., "Antisense intronic non-coding RNA levels correlate to the degree of tumor differentiation in prostate cancer," Oncogene (2004) 23(39):6684-6692.

Rhodes et al., "Multiplex biomarker approach for determining risk of prostatespecific antigen-defined recurrence of prostate cancer," J Nat Cancer Inst. (May 7, 2003) vol. 95, No. 9, pp. 661-668.

Rinn et al., "Functional demarcation of active and silent chromatin domains in human HOX loci by noncoding RNAs," Cell (Jun. 29, 2007) 129(7):1311-23.

Robinson et al., "A dynamic programming approach for the alignment of signal peaks in multiple gas chromatography-mass spectrometry experiments," BMC Bioinformatics (2007) 8.1:419.

Rotblat et al., "A Possible Role for Long Non-Coding RNA in Modulating Signaling Pathways," Med. Hvnotheses (2011), 77:962-965, Elsevier.

Sanghvi, "Heterocyclic base modifications in nucleic acids and their applications in antisense oligonucleotides in Antisense Research and Applications," Crooke, S. T. and Lebleu, B., ed., CRC Press. (1993) Ch 15 274-285.

Sato et al., "Clinical significance of alterations of chromosome 8 in high-grade, advanced, nonmetastatic prostate carcinoma," J Natl Cancer Inst. (1999) 91:1574-1580.

Shariat et al., "Survivin expression is associated with features of biologically aggressive prostate carcinoma," Cancer (2004) 100(4): 751-757.

Shariat et al., "An updated catalog of prostate cancer predictive tools," Cancer 2008, 113(11):3062-6.

Shen et al., "The SWI/SNF ATPase Brm is a gatekeeper of proliferative control in prostate cancer." Cancer Res. (Dec. 15, 2008) 68(24):10154-62.

Shibru et al., "Does the 3-gene diagnostic assay accurately distinguish benign from malignant thyroid neoplasms?" Cancer (Sep. 1, 2008) 113(5):930-935. doi: 10.1002/cncr.23703.

Simmons et al., "Natural history of biochemical recurrence after radical prostatectomy: risk assessment for secondary herapy," Eur Urol. (May 2007) 51(5):1175-84.

Singh et al., "Synthesis of 2'-amino-LNA: A novel conformationally restricted high-affinity oligonucleotide analogues with a handle," J Bio Chem (1998) 63:10035-10039.

Singh et al., "LNA (locked nucleic acids): synthesis and high-affinity nucleic acid recognition," Chem Commun (1998) 4:455-456.

(56) References Cited

OTHER PUBLICATIONS

Srikantan et al., "PCGEM1, a prostate-specific gene, is overexpressed in prostate cancer," PNAS (Oct. 24, 2000) 97(22): 12216-12221.

Taft et al., "Non-coding RNAs: regulators of disease," J Pathol. (Jan 2010) 220(2):126-39.

Taylor et al., "Integrative genomic profiling of human prostate cancer", Cancer Cell (Jul. 13, 2010) vol. 18 (1), pp. 11-22.

Thompson et al., "Adjuvant and Salvage Radiotherapy After Prostatectomy: AUA/ASTRO Guideline," J Urol. (2013) 190(2):441-9.

Thorsen et al., "Alternative Splicing in Colon, Bladder, and Prostate Cancer Identified by Exon Array Analysis," Molecular & Cellular Proteomics (Mar. 18, 2008) vol. 7, No. 7, pp. 1214-1224.

Tomlins et al., "Distinct classes of chromosomal rearrangements create oncogenic ETS gene fusions in prostate cancer." Nature (Aug. 2, 2007) 448(7153):595-9.

True et al., "A molecular correlate to the Gleason grading system for prostate ladenocarcinoma," Proc Nat Acad Sci U S A. (Jul. 18, 2006) 103(29): 10991-6. Epub Jul. 7, 2006 preceding development of malignancy, J Clin Oncol. (Jul. 15, 2004) 22(14):2790-9.

Varela et al., "Exome sequencing identifies frequent mutation of the SWI/SNF complex gene PBRM1 in renal carcinoma," Nature (Jan. 27, 2011) 469(7331):539-42.

Varricchi et al., "Are Mast Cells MASTers in Cancer?" Front Immunol. ePub (Apr. 12, 2017) 8:424.

Vickers et al., "Extensions to decision curve analysis, a novel method for evaluating diagnostic tests, prediction models and molecular markers," BMC Medical Informatics and Decision Making, (2008) 8(53):1-17.

Wang et al., "RNA-Seq: a revolutionary tool for transcriptomics," Nature Reviews/Genetics (Jan. 2009) vol. 10, pp. 57-63.

Weber et al., "The prognostic value of expression of HIF1 [alpha], EGFR and VEGF-A, in localized prostate cancer for intermediate— and high-risk patients treated with radiation therapy with or without androgen deprivation therapy"; Radiation Oncology (Apr. 30, 2012) vol. 7, No. 66, 8 pages.

Wiegand et al., "ARID1A mutations in endometriosis-associated ovarian carcinomas", N Engl J Med. (Oct. 14, 2010) 363 (16):1532-43.

Yap et al., "Molecular interplay of the noncoding RNA ANRIL and methylated histone H3 lysine 27 by polycomb CBX7 n transcriptional silencing of INK4a", Mol Cell. (Jun. 11, 2010) 38(5):662-74.

Yates et al., "X:Map: annotation and visualization of genome structure for Affymetrix exon array analysis," Nucleic Acids Res., (2008) vol. 36:D780-D786.

Yegnasubramanian et al., "DNA hypomethylation arises later in prostate cancer progression than CpG island hypermethylation and contributes to metastatic tumor heterogeneity", Cancer Res. (Nov. 1, 2008) 68(21): pp. 8954-8967.

Yu et al., "An integrated network of androgen receptor, polycomb, and TMPRSS2-ERG gene fusions in prostate cancer progression," Cancer Cell. (May 18, 2010) 17(5):443-54.

Yukinawa et al., "A multi-class predictor based on a probabilistic model: application to gene expression profiling-based diagnosis of thyroid tumors," BMC Genomics (Jul. 27, 2006) 7:190.

Zelefsky et al., "High dose radiation delivered by intensity modulated conformal radiotherapy improves the outcome of localized prostate cancer," The Journal of Urology (Sep. 2001) 166(3):876-881.

Zhao et al., "Development and validation of a 24-gene predictor of response to postoperative radiotherapy in prostate cancer: a matched, retrospective analysis," Lancet Oncol (2016) 17, pp. 1612-20.

\* cited by examiner

A

B

SEQUENCE LISTING

<160> NUMBER OF SEQ ID NOS: 47

<210> SEQ ID NO 1
<211> LENGTH: 49
<212> TYPE: DNA
<213> ORGANISM: Homo sapiens

<400> SEQUENCE: 1
gggataagaa gctaaccaaa gcccatgtgt tcgagtgtaa tttagagag         49

<210> SEQ ID NO 2
<211> LENGTH: 46
<212> TYPE: DNA
<213> ORGANISM: Homo sapiens

<400> SEQUENCE: 2
gaggaaaatc gggaagcagc ttataatgcc attactttac ctgaag            46

<210> SEQ ID NO 3
<211> LENGTH: 47
<212> TYPE: DNA
<213> ORGANISM: Homo sapiens

<400> SEQUENCE: 3
tgattttgga atggatgatc gtgagataat gagagaaggc agtgctt           47

<210> SEQ ID NO 4
<211> LENGTH: 50
<212> TYPE: DNA
<213> ORGANISM: Homo sapiens

<400> SEQUENCE: 4
tgagtttgac tcatcagatg aagagcctat tgaagatgaa cagactccaa        50

<210> SEQ ID NO 5
<211> LENGTH: 46
<212> TYPE: DNA
<213> ORGANISM: Homo sapiens

```
<400> SEQUENCE: 5
tcctgacata gccagctgct gtgaaataat ggaagagctt acaacc              46

<210> SEQ ID NO 6
<211> LENGTH: 47
<212> TYPE: DNA
<213> ORGANISM: Homo sapiens

<400> SEQUENCE: 6
ttcgggacaa attagctgca catctatcat caagagattc acaatca             47

<210> SEQ ID NO 7
<211> LENGTH: 44
<212> TYPE: DNA
<213> ORGANISM: Homo sapiens

<400> SEQUENCE: 7
tgcagctggt tggtgtcact gccatgttta ttgcaagcaa atat                44

<210> SEQ ID NO 8
<211> LENGTH: 48
<212> TYPE: DNA
<213> ORGANISM: Homo sapiens

<400> SEQUENCE: 8
aacaagtatg ccacatcgaa gcatgctaag atcagcactc taccacag            48

<210> SEQ ID NO 9
<211> LENGTH: 47
<212> TYPE: DNA
<213> ORGANISM: Homo sapiens

<400> SEQUENCE: 9
tttagccaag gctgtggcaa aggtgtaact tgtaaacttg agttgga             47

<210> SEQ ID NO 10
<211> LENGTH: 47
<212> TYPE: DNA
<213> ORGANISM: Homo sapiens

<400> SEQUENCE: 10
catggtgcaa aaataccagt ccccagtgag agtgtacaaa tacccct             47

<210> SEQ ID NO 11
<211> LENGTH: 44
<212> TYPE: DNA
<213> ORGANISM: Homo sapiens

<400> SEQUENCE: 11
tcctttgatt ccgatgttcg tgggcagtga cactgtgagt gaat                44

<210> SEQ ID NO 12
<211> LENGTH: 48
<212> TYPE: DNA
<213> ORGANISM: Homo sapiens

<400> SEQUENCE: 12
caccctgaaa atgaagattg gacctgtttt gaacagtctg caagttta            48

<210> SEQ ID NO 13
<211> LENGTH: 48
<212> TYPE: DNA
<213> ORGANISM: Homo sapiens
```

<400> SEQUENCE: 13
catgattgag caagtgcatg actgtgaaat cattcatgga gacattaa                48

<210> SEQ ID NO 14
<211> LENGTH: 47
<212> TYPE: DNA
<213> ORGANISM: Homo sapiens

<400> SEQUENCE: 14
cttggaaacg gattttggga acaggatgat gaagatgatt tatctgc                 47

<210> SEQ ID NO 15
<211> LENGTH: 46
<212> TYPE: DNA
<213> ORGANISM: Homo sapiens

<400> SEQUENCE: 15
tgagatgctc agcaacaaac catggaacta ccagatcgat tacttt                  46

<210> SEQ ID NO 16
<211> LENGTH: 47
<212> TYPE: DNA
<213> ORGANISM: Homo sapiens

<400> SEQUENCE: 16
cagactccct catcaccaaa aagcaagtgt cagtctggtg cagtaat                 47

<210> SEQ ID NO 17
<211> LENGTH: 45
<212> TYPE: DNA
<213> ORGANISM: Homo sapiens

<400> SEQUENCE: 17
caggcctttc tgcagaaagc aggcaaatct ctgttgttct atgcc                   45

<210> SEQ ID NO 18
<211> LENGTH: 46
<212> TYPE: DNA
<213> ORGANISM: Homo sapiens

<400> SEQUENCE: 18
ttccaggaca tcatgcaaaa gcaaagacca gaaagagtgt ctcatc                  46

<210> SEQ ID NO 19
<211> LENGTH: 48
<212> TYPE: DNA
<213> ORGANISM: Homo sapiens

<400> SEQUENCE: 19
aatgccatca ttgctgaaact tttgagactc tctgagttta ttcctgct               48

<210> SEQ ID NO 20
<211> LENGTH: 48
<212> TYPE: DNA
<213> ORGANISM: Homo sapiens

<400> SEQUENCE: 20
tgggaaagca aactggatgc taagccagag ctacaggatt tagatgaa                48

<210> SEQ ID NO 21
<211> LENGTH: 45
<212> TYPE: DNA
<213> ORGANISM: Homo sapiens

<400> SEQUENCE: 21
caaccaggtg ccaaaagacc atccaactat cccgagagct atttc        45

<210> SEQ ID NO 22
<211> LENGTH: 47
<212> TYPE: DNA
<213> ORGANISM: Homo sapiens

<400> SEQUENCE: 22
tttggttccc ttgtgttgat tcatactctg aattgtgtac atggaaa      47

<210> SEQ ID NO 23
<211> LENGTH: 46
<212> TYPE: DNA
<213> ORGANISM: Homo sapiens

<400> SEQUENCE: 23
tttcccacag ttgcaaactt gaatagaatc aagttgaaca gcaaac       46

<210> SEQ ID NO 24
<211> LENGTH: 47
<212> TYPE: DNA
<213> ORGANISM: Homo sapiens

<400> SEQUENCE: 24
ggcagagaga ggtgctcatg ttttctcttg tgggtatcaa aattcta      47

<210> SEQ ID NO 25
<211> LENGTH: 45
<212> TYPE: DNA
<213> ORGANISM: Homo sapiens

<400> SEQUENCE: 25
ccatccctcg aactcaagtc ccgctcatta caaattcttc ttgcc        45

<210> SEQ ID NO 26
<211> LENGTH: 44
<212> TYPE: DNA
<213> ORGANISM: Homo sapiens

<400> SEQUENCE: 26
aagagaggct gcaggaacag cggagaacag ttcaggacaa gaag         44

<210> SEQ ID NO 27
<211> LENGTH: 44
<212> TYPE: DNA
<213> ORGANISM: Homo sapiens

<400> SEQUENCE: 27
ccaaaccagc cagtcccaag aagaacatta aaactaggag tgcc         44

<210> SEQ ID NO 28
<211> LENGTH: 42
<212> TYPE: DNA
<213> ORGANISM: Homo sapiens

<400> SEQUENCE: 28
caacaaggcc ctgagcgtgg gtaacatcga tgatgcctta ca           42

<210> SEQ ID NO 29
<211> LENGTH: 47
<212> TYPE: DNA
<213> ORGANISM: Homo sapiens

<400> SEQUENCE: 29
tcatgaaccc tttcaacatg cctaatctgt atcagaagtt ggagagt        47

<210> SEQ ID NO 30
<211> LENGTH: 47
<212> TYPE: DNA
<213> ORGANISM: Homo sapiens

<400> SEQUENCE: 30
aaaaagagct ggggaacgat gcctacaaga agaaagactt tgacaca        47

<210> SEQ ID NO 31
<211> LENGTH: 47
<212> TYPE: DNA
<213> ORGANISM: Homo sapiens

<400> SEQUENCE: 31
cctggacacc caactacaag cagtgttcat ggagttcatt gaattat        47

<210> SEQ ID NO 32
<211> LENGTH: 45
<212> TYPE: DNA
<213> ORGANISM: Homo sapiens

<400> SEQUENCE: 32
agaaatgcat gctgtcagcg ttggtatttc acattcaatg gagct        45

<210> SEQ ID NO 33
<211> LENGTH: 47
<212> TYPE: DNA
<213> ORGANISM: Homo sapiens

<400> SEQUENCE: 33
accaaggaag ccctgaaatg aattcaacaa ttaatattca tcgcact        47

<210> SEQ ID NO 34
<211> LENGTH: 47
<212> TYPE: DNA
<213> ORGANISM: Homo sapiens

<400> SEQUENCE: 34
cagtcctgtt cagaatgagc aaggctttgt ggagttcaaa atttctg        47

<210> SEQ ID NO 35
<211> LENGTH: 46
<212> TYPE: DNA
<213> ORGANISM: Homo sapiens

<400> SEQUENCE: 35
caatagcaac aggtgcagca gcaagactag tgtcaggata cgacag        46

<210> SEQ ID NO 36
<211> LENGTH: 46
<212> TYPE: DNA
<213> ORGANISM: Homo sapiens

<400> SEQUENCE: 36
gatccatgca acctggactt gataaaccgg aagattaagt ctgtag        46

<210> SEQ ID NO 37
<211> LENGTH: 45
<212> TYPE: DNA
<213> ORGANISM: Homo sapiens

<400> SEQUENCE: 37
cagcctccac attcagaggc atcacaagta atggcacaat tcttc    45

<210> SEQ ID NO 38
<211> LENGTH: 46
<212> TYPE: DNA
<213> ORGANISM: Homo sapiens

<400> SEQUENCE: 38
ttctgaaaca agggcgtgga tccctcaacc aagaagaatg tttatg    46

<210> SEQ ID NO 39
<211> LENGTH: 47
<212> TYPE: DNA
<213> ORGANISM: Homo sapiens

<400> SEQUENCE: 39
tgcttgggga ctattggaga aaataaggtg gagtcctact tgtttaa    47

<210> SEQ ID NO 40
<211> LENGTH: 47
<212> TYPE: DNA
<213> ORGANISM: Homo sapiens

<400> SEQUENCE: 40
agtgcctatg gaacatccag ctgataatct tgcctagtaa gagcaaa    47

<210> SEQ ID NO 41
<211> LENGTH: 46
<212> TYPE: DNA
<213> ORGANISM: Homo sapiens

<400> SEQUENCE: 41
ttctggcacc atttcgtagc cattctcttt gtattttaaa aggacg    46

<210> SEQ ID NO 42
<211> LENGTH: 47
<212> TYPE: DNA
<213> ORGANISM: Homo sapiens

<400> SEQUENCE: 42
cctcaaagaa accatggcca gtagctaggt gttcagtagg aatcaaa    47

<210> SEQ ID NO 43
<211> LENGTH: 47
<212> TYPE: DNA
<213> ORGANISM: Homo sapiens

<400> SEQUENCE: 43
ttgcacacct gttagcaaga aacagaagtt gaaggactgg aacaagt    47

<210> SEQ ID NO 44
<211> LENGTH: 47
<212> TYPE: DNA
<213> ORGANISM: Homo sapiens

<400> SEQUENCE: 44
tcctgtgaaa tctccgagga gaagaaagaa tgatggacag tttatcc    47

<210> SEQ ID NO 45
<211> LENGTH: 48
<212> TYPE: DNA
<213> ORGANISM: Homo sapiens

```
<400> SEQUENCE: 45
gcagcattaa gaggtcttct gggagcctta acaagtaccc catattct                48

<210> SEQ ID NO 46
<211> LENGTH: 48
<212> TYPE: DNA
<213> ORGANISM: Homo sapiens

<400> SEQUENCE: 46
gaattcggaa cagatctaac ccaaaagtac tttctgagaa gcagaatg                48

<210> SEQ ID NO 47
<211> LENGTH: 44
<212> TYPE: DNA
<213> ORGANISM: Homo sapiens

<400> SEQUENCE: 47
aggggtctca tgtggtcctc ctcgctatgt tggaaatgtg caac                    44
```

BIOMARKER PANELS FOR PREDICTING PROSTATE CANCER OUTCOMES

CROSS-REFERENCE TO RELATED APPLICATIONS

This application is a continuation application of U.S. application Ser. No. 12/747,879, filed May 29, 2009, now pending, which claims the benefit of priority to U.S. Provisional Application Ser. No. 61/057,698, filed May 30, 2008. The disclosures of the prior applications are considered part of (and are incorporated by reference in) the disclosure of this application.

SEQUENCE LISTING

The present application is being filed along with a Sequence Listing in electronic format. The Sequence Listing is provided as a file entitled 2018-07-02_sequence_listing-GENDX.009C1, created Jul. 2, 2018, which is 6.69 Kb in size. The information in the electronic format of the Sequence Listing is incorporated herein by reference in its entirety.

STATEMENT AS TO FEDERALLY SPONSORED RESEARCH

Funding for the work described herein was provided by the federal government under grant number 90966043 awarded by the National Institute of Health. The federal government has certain rights in the invention.

BACKGROUND

1. Technical Field

This document relates to methods and materials involved in predicting the outcome of prostate cancer.

2. Background Information

Prostate cancer occurs when a malignant tumor forms in the tissue of the prostate. The prostate is a gland in the male reproductive system located below the bladder and in front of the rectum. The main function of the prostate gland, which is about the size of a walnut, is to make fluid for semen. Although there are several cell types in the prostate, nearly all prostate cancers start in the gland cells. This type of cancer is known as adenocarcinoma.

Prostate cancer is the second leading cause of cancer-related death in American men. Most of the time, prostate cancer grows slowly. Autopsy studies show that many older men who died of other diseases also had prostate cancer that neither they nor their doctor were aware of Sometimes, however, prostate cancer can grow and spread quickly. It is important to be able to distinguish prostate cancers that will grow slowly from those that will grow quickly since treatment can be especially effective when the cancer has not spread beyond the region of the prostate. Finding ways to detect cancers early can improve survival rates.

SUMMARY

This document provides methods and materials related to assessing male mammals (e.g., humans) with prostate cancer. For example, this document provides methods and materials for predicting (1) which patients, at the time of PSA reoccurrence, will later develop systemic disease, (2) which patients, at the time of retropubic radial prostatectomy, will later develop systemic disease, and (3) which patients, at the time of systemic disease, will later die from prostate cancer.

The majority of men with prostate cancer are diagnosed with cancers with low mortality. Initial treatment is typically radical prostatectomy, external beam radiotherapy, or brachytherapy and followed by serial serum PSA measurements. Not every man who suffers PSA recurrence is destined to suffer systemic progression or to die of his prostate cancer. Thus, it is not clear whether men with PSA recurrence should be simply observed or should receive early androgen ablation. The methods and materials provided herein can be used to predict which men with a rising PSA post-definitive therapy might benefit from additional therapy.

In general, one aspect of this document features a method for predicting whether or not a human, at the time of PSA reoccurrence or retropubic radial prostatectomy, will later develop systemic disease. The method comprises, or consists essentially of, (a) determining an expression profile score for cancer tissue from the human, wherein the expression profile score is based on at least the expression levels of RAD21, CDKN3, CCNB1, SEC14L1, BUB1, ALAS1, KIAA0196, TAF2, SFRP4, STIP1, CTHRC1, SLC44A1, IGFBP3, EDG7, FAM49B, C8orf53, and CDK10 nucleic acid, and (b) prognosing the human as later developing systemic disease or as not later developing systemic disease based on at least the expression profile score. The method can be performed at the time of the PSA reoccurrence. The method can be performed at the time of the retropubic radial prostatectomy. The expression levels can be mRNA expression levels. The prognosing step (b) can comprise prognosing the human as later developing systemic disease or as not later developing systemic disease based on at least the expression profile score and a clinical variable. The clinical variable can be selected from the group consisting of a Gleason score and a revised Gleason score. The clinical variable can be selected from the group consisting of a Gleason score, a revised Gleason score, the pStage, age at surgery, initial PSA at recurrence, use of hormone or radiation therapy after radical retropubic prostatectomy, age at PSA recurrence, the second PSA level at time of PSA recurrence, and PSA slope. The method can comprise prognosing the human as later developing systemic disease based on at least the expression profile score. The method can comprise prognosing the human as not later developing systemic disease based on at least the expression profile score.

In another aspect, this document features a method for predicting whether or not a human, at the time of systemic disease, will later die from prostate cancer. The method comprises, or consists essentially of, (a) determining an expression profile score for cancer tissue from the human, wherein the expression profile score is based on at least the expression levels of RAD21, CDKN3, CCNB1, SEC14L1, BUB1, ALAS1, KIAA0196, TAF2, SFRP4, STIP1, CTHRC1, SLC44A1, IGFBP3, EDG7, FAM49B, C8orf53, and CDK10 nucleic acid, and (b) prognosing the human as later dying of the prostate cancer or as not later dying of the prostate cancer based on at least the expression profile score. The expression levels can be mRNA expression levels. The prognosing step (b) can comprise prognosing the human as later developing systemic disease or as not later developing systemic disease based on at least the expression profile score and a clinical variable. The clinical variable can be selected from the group consisting of a Gleason score and a revised Gleason score. The clinical variable can be selected from the group consisting of a Gleason score, a revised Gleason score, the pStage, age at surgery, initial PSA at recurrence, use of hormone or radiation therapy after radical retropubic prostatectomy, age at PSA recurrence, the second PSA level at time of PSA recurrence, and PSA slope. The method can comprise prognosing the human as later dying of the prostate cancer based on at least the expression profile score. The method can comprise prognosing the human as not later dying of the prostate cancer based on at least the expression profile score.

In another aspect, this document features a method for (1) predicting whether or not a patient, at the time of PSA reoccurrence, will later develop systemic disease, (2) predicting whether or not a patient, at the time of retropubic radial prostatectomy, will later develop systemic disease, or (3) predicting whether or not a patient, at the time of systemic disease, will later die from prostate cancer. The method comprises, or consists essentially of, determining whether or not cancer tissue from the patient contains an RAD21, CDKN3, CCNB1, SEC14L1, BUB1, ALAS1, KIAA0196, TAF2, SFRP4, STIP1, CTHRC1, SLC44A1, IGFBP3, EDG7, FAM49B, C8orf53, and CDK10 expression profile indicative of a later development of the systemic disease or the death.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
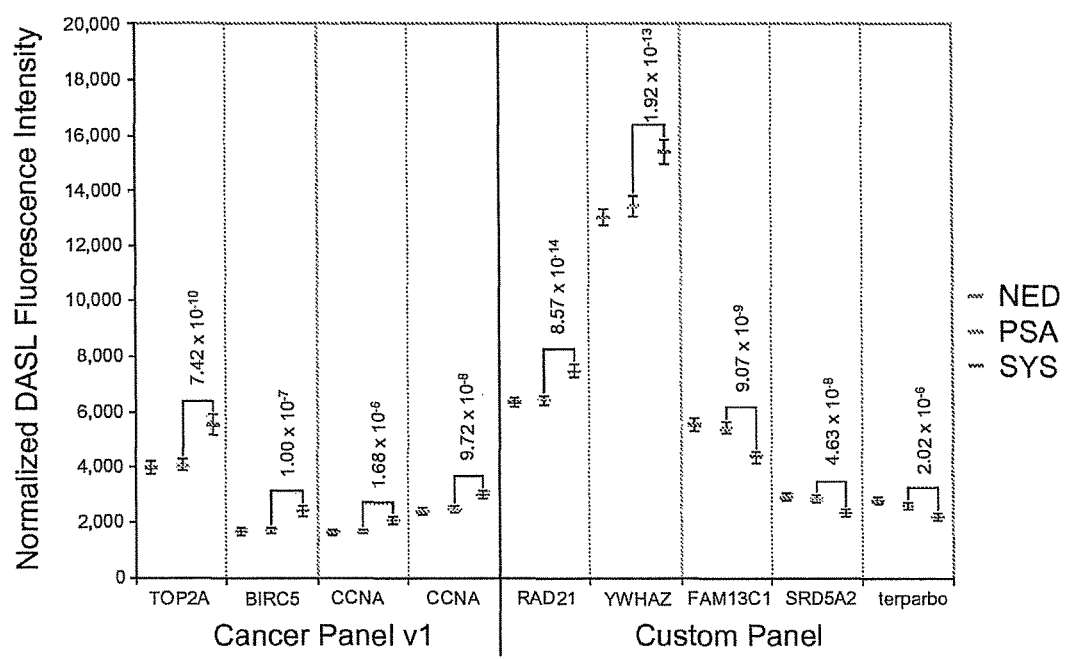
FIG. 1: Nine genes with significantly different expression in cases with systemic disease progression (SYS) versus controls with PSA recurrence (PSA). P-values (t-test) for the SYS case/PSA control comparison are shown. Controls with no evidence of disease recurrence (NED) are also included.

This document provides methods and materials related to assessing male mammals (e.g., humans) with prostate cancer. For example, this document provides methods and materials for predicting (1) which patients, at the time of PSA reoccurrence, will later develop systemic disease, (2) which patients, at the time of retropubic radial prostatectomy, will later develop systemic disease, and (3) which patients, at the time of systemic disease, will later die from prostate cancer. As described herein, the expression level of any of the genes listed in the tables provided herein (e.g., Tables 2 and 3) or any combination of the genes listed in the tables provided herein can be assessed as described herein to predict (1) which patients, at the time of PSA reoccurrence, will later develop systemic disease, (2) which patients, at the time of retropubic radial prostatectomy, will later develop systemic disease, and (3) which patients, at the time of systemic disease, will later die from prostate cancer. For example, the combination of genes set forth in Table 3 can be assessed as described herein to predict (1) which patients, at the time of PSA reoccurrence, will later develop systemic disease, (2) which patients, at the time of retropubic radial prostatectomy, will later develop systemic disease, and (3) which patients, at the time of systemic disease, will later die from prostate cancer.

Any appropriate type of sample (e.g., cancer tissue) can be used to assess the level of gene expression. For example, prostate cancer tissue can be collected and assessed to determine the expression level of a gene listed in any of the tables provided herein. Once obtained, the expression level for a particular nucleic acid can be used as a raw number or can be normalized using appropriate calculations and controls. In addition, the expression levels for groups of nucleic acids can be combined to obtain an expression level score that is based on the measured expression levels (e.g., raw expression level number or normalized number). In some cases, the expression levels of the individual nucleic acids that are used to obtain an expression level score can be weighted. An expression level score can be a whole number, an integer, an alphanumerical value, or any other representation capable of indicating whether or not a condition is met. In some cases, an expression level score is a number that is based on the mRNA expression levels of at least the seventeen nucleic acids listed in Table 3. In some cases, an expression level score can be based on the mRNA expression levels of the seventeen nucleic acids listed in Table 3 and no other nucleic acids. As described herein, the seventeen nucleic acids listed in Table 3 can be used together to determine, at the time of PSA reoccurrence or at the time of retropubic radial prostatectomy, whether or not a mammal will later develop systemic disease. In addition, the seventeen nucleic acids listed in Table 3 can be used together to determine, at the time of systemic disease, whether or not a mammal will later die of prostate cancer.

For humans, the seventeen nucleic acids listed in Table 3 can have the nucleic acid sequence set forth in GenBank as follows: RAD21 (GenBank Accession No. NM_006265; GI No. 208879448; probe sequences GGGATAAGAAGCTAACCAAAGCCCATGTGTTCGAGTGTAATTTAGAGAG (SEQ ID NO:1), GAGGAAAATCGGGAAGCAGCTTATAATGCCATTACTTTACCTGAAG (SEQ ID NO:2), and TGATTTTGGAATGGATGATCGTGAGATAATGAGAGAAGGCAGTGCTT (SEQ ID NO:3)), CDKN3 (GenBank Accession Nos. NM_005192 and NM_001130851; GI Nos. 195927023 and 195927024; probe sequences TGAGTTTGACTCATCAGATGAAGAGCCTATTGAAGATGAACAGACTCCAA (SEQ ID NO:4), TCCTGACATAGCCAGCTGCTGTGAAATAATGGAAGAGCTTACAACC (SEQ ID NO:5), and TTCGGGACAAATTAGCTGCACATCTATCATCAAGAGATTCACAATCA (SEQ ID NO:6)), CCNB1 (GenBank Accession No. NM_031966; GI No. 34304372; probe sequences TGCAGCTGGTTGGTGTCACTGCCATGTTTATTGCAAGCAAATAT (SEQ ID NO:7), AACAAGTATGCCACATCGAAGCATGCTAAGATCAGCACTCTACCACAG (SEQ ID NO:8), and TTTAGCCAAGGCTGTGGCAAAGGTGTAACTTGTAAACTTGAGTTGGA (SEQ ID NO:9)), SEC14L1 (GenBank Accession Nos. NM_001039573, NM_001143998, NM_001143999, NM_001144001, and NM_003003; GI Nos. 221316683, 221316675, 221316679, 221316686, and 221316681; probe sequences CATGGTGCAAAAATACCAGTCCCCAGTGAGAGTGTACAAATACCCCT (SEQ ID NO:10), TCCTTTGATTCCGATGTTCGTGGGCAGTGACACTGTGAGTGAAT (SEQ ID NO:11), and CACCCTGAAAATGAAGATTGGACCTGTTTTGAACAGTCTGCAAGTTTA (SEQ ID NO:12)), BUB1 (GenBank Accession No. NM 004336; GI No. 211938448; probe sequences CATGATTGAGCAAGTGCATGACTGTGAAATCATTCATGGAGACATTAA (SEQ ID NO:13), CTTGGAAACGGATTTTTGGAACAGGATGATGAAGATGATTTATCTGC (SEQ ID NO:14), and TGAGATGCTCAGCAACAAACCATGGAACTACCAGATCGATTACTTT (SEQ ID NO:15)), ALAS1 (GenBank Accession Nos. NM_000688 and NM_199166; GI Nos. 40316942 and 40316938; probe sequences CAGACTCCCTCATCACCAAAAAGCAAGTGTCAGTCTGGTGCAGTAAT (SEQ ID NO:16), CAGGCCTTTCTGCAGAAAGCAGGCAAATCTCTGTTGTTCTATGCC (SEQ ID NO:17), and TTCCAGGACATCATGCAAAAGCAAAGACCAGAAAGAGTGTCTCATC (SEQ ID NO:18)), KIAA0196 (GenBank Accession No. NM_014846; GI No. 120952850; probe sequences AATGCCATCATTGCTGAACTTTTGAGACTCTCTGAGTTTATTCCTGCT (SEQ ID NO:19), TGGGAAAGCAAACTGGATGCTAAGCCAGAGCTACAGGATTTAGATGAA (SEQ ID NO:20), and CAACCAGGTGCCAAAAGACCATCCAACTATCCCGAGAGCTATTTC (SEQ ID NO:21)), TAF2 (GenBank Accession No. NM_003184; GI No. 115527086; probe sequences TTTGGTTCCCTTGTGTTGATTCATACTCTGAATTGTGTACATGGAAA (SEQ ID NO:22), TTTCCCACAGTTGCAAACTTGAATAGAATCAAGTTGAACAGCAAAC (SEQ ID NO:23), and GGCAGAGAGAGGTGCTCATGTTTTCTGTGTGGGTATCAAAATTCTA (SEQ ID NO:24)), SFRP4 (GenBank Accession No. NM_003014; GI No. 170784837; probe sequences CCATCCCTCGAACTCAAGTCCCGCTCATTACAAATTCTTCTTGCC (SEQ ID NO:25), AAGAGAGGCTGCAGGAACAGCGGAGAACAGTTCAGGACAAGAAG (SEQ ID NO:26), and CCAAACCAGCCAGTCCCAAGAAGAACATTAAAACTAGGAGTGCC (SEQ ID NO:27)), STIP1 (GenBank Accession No. NM_006819; GI No. 110225356; probe sequences CAACAAGGCCCTGAGCGTGGGTAACATCGATGATGCCTTACA (SEQ ID NO:28), TCATGAACCCTTTCAACATGCCTAATCTGTATCAGAAGTTGGAGAGT (SEQ ID NO:29), and AAAAAGAGCTGGGGAACGATGCCTACAAGAAGAAAGACTTTGACACA (SEQ ID NO:30)), CTHRC1 (GenBank Accession No. NM_138455; GI No. 34147546; probe sequences CCTGGACACCCAACTACAAGCAGTGTTCATGGAGTTCATTGAATTAT (SEQ ID NO:31), AGAAATGCATGCTGTCAGCGTTGGTATTTCACATTCAATGGAGCT (SEQ ID NO:32), ACCAAGGAAGCCCTGAAATGAATTCAACAATTAATATTCATCGCACT (SEQ ID NO:33)), SLC44A1 (GenBank Accession No. NM_080546; GI No. 112363101; probe sequences CAGTCCTGTTCAGAATGAGCAAGGCTTTGTGGAGTTCAAAATTTCTG (SEQ ID NO:34), CAATAGCAACAGGTGCAGCAGCAAGACTAGTGTCAGGATACGACAG (SEQ ID NO:35), and GATCCATGCAACCTGGACTTGATAAACCGGAAGATTAAGTCTGTAG (SEQ ID NO:36)), IGFBP3 (GenBank Accession Nos. NM_000598 and NM_001013398; GI Nos. 62243067 and 62243247; probe sequences CAGCCTCCACATTCAGAGGCATCACAAGTAATGGCACAATTCTTC (SEQ ID NO:37), TTCTGAAACAAGGGCGTGGATCCCTCAACCAAGAAGAATGTTTATG (SEQ ID NO:38), and TGCTTGGGGACTATTGGAGAAAATAAGGTGGAGTCCTACTTGTTTAA (SEQ ID NO:39)), EDG7 (GenBank Accession No. NM_012152; GI No. 183396778; probe sequences AGTGCCTATGGAACATCCAGCTGATAATCTTGCCTAGTAAGAGCAAA (SEQ ID NO:40), TTCTGGCACCATTTCGTAGCCATTCTCTTTGTATTTTAAAAGGACG (SEQ ID NO:41), and CCTCAAAGAAACCATGGCCAGTAGCTAGGTGTTCAG- TAGGAATCAAA (SEQ ID NO:42)), FAM49B (GenBank Accession No. NM_016623; GI No. 42734437; probe sequences TTGCACACCTGTTAGCAAGAAACA-GAAGTTGAAGGACTGGAACAAGT (SEQ ID NO:43), TCCTGTGAAATCTCCGAGGAGAAGAAAGAAT-GATGGACAGTTTATCC (SEQ ID NO:44), and GCAG-CATTAAGAGGTCTTCTGGGAGCCTTAACAAGTAC-CCCATATTCT (SEQ ID NO:45)), C8orf53 (GenBank Accession No. NM_032334; GI No. 223468686; probe sequence GAATTCGGAACAGATCTAACCCAAAAG-TACTTTCTGAGAAGCAGAATG (SEQ ID NO:46)), and CDK10 (GenBank Accession Nos. NM_001098533, NM_001160367, NM_052987, and NM_052988; GI Nos. 237858579, 237858581, 237858574, and 237858573; probe sequence AGGGGTCTCATGTGGTCCTCCTCGCTATGT-TGGAAATGTGCAAC (SEQ ID NO:47)).

Any appropriate method can be used to determine the expression level of a gene listed herein. For example, reverse transcription-PCR (RT-PCR) techniques can be performed to detect the level of gene expression.

The term "elevated level" as used herein with respect to the level of mRNA for a nucleic acid listed herein is any mRNA level that is greater than a reference mRNA level for that nucleic acid. The term "reference level" as used herein with respect to an mRNA for a nucleic acid listed herein is the level of mRNA for a nucleic acid listed herein that is typically expressed by mammals with prostate cancer that does not progress to systemic disease or result in prostate cancer-specific death. For example, a reference level of an mRNA biomarker listed herein can be the average mRNA level of that biomarker that is present in samples obtained from a random sampling of 50 males without prostate cancer.

It will be appreciated that levels from comparable samples are used when determining whether or not a particular level is an elevated level. For example, the average mRNA level present in bulk prostate tissue from a random sampling of mammals may be X units/g of prostate tissue, while the average mRNA level present in isolated prostate epithelial cells may be Y units/number of prostate cells. In this case, the reference level in bulk prostate tissue would be X units/g of prostate tissue, and the reference level in isolated prostate epithelial cells would be Y units/number of prostate cells. Thus, when determining whether or not the level in bulk prostate tissue is elevated, the measured level would be compared to the reference level in bulk prostate tissue. In some cases, the reference level can be a ratio of an expression value of a biomarker in a sample to an expression value of a control nucleic acid or polypeptide in the sample. A control nucleic acid or polypeptide can be any polypeptide or nucleic acid that has a minimal variation in expression level across various samples of the type for which the nucleic acid or polypeptide serves as a control. For example, GAPDH, HPRT, NDUFA7, and RPS16 nucleic acids or polypeptides can be used as control nucleic acids or polypeptides, respectively, in prostate samples. In some cases, nucleic acids or polypeptides can be used as control nucleic acids or polypeptides, respectively, as described elsewhere (Ohl et al., *J. Mol. Med.*, 83:1014-1024 (2005)).

Once determined, the level of mRNA expression for a particular nucleic acid listed herein (or the degree of which the level is elevated over a reference level) can be combined with the levels of mRNA expression for other particular nucleic acids listed herein to obtain an expression level score. For example, the mRNA levels for each nucleic acid listed in Table 3 can be added together to obtain an expression level score. If this expression level score is greater than the sum of corresponding mRNA reference levels for each nucleic acid listed in Table 3, then the patient, at the time of PSA reoccurrence or retropubic radial prostatectomy, can be classified as later developing systemic disease or, at the time of systemic disease, can be classified as later dying from prostate cancer.

In some cases, the levels of biomarkers (e.g., an expression level score) can be used in combination with one or more other factors to assess a prostate cancer patient. For example, expression level scores can be used in combination with the clinical stage, the serum PSA level, and/or the Gleason score of the prostate cancer to determine, at the time of PSA reoccurrence or at the time of retropubic radial prostatectomy, whether or not a mammal will later develop systemic disease. In addition, such combinations can be used together to determine, at the time of systemic disease, whether or not a mammal will later die of prostate cancer. Additional information about the mammal, such as information concerning genetic predisposition to develop cancer, SNPs, chromosomal abnormalities, gene amplifications or deletions, and/or post translational modifications, can also be used in combination with the level of one or more biomarkers provided herein (e.g., the list of nucleic acids set forth in Table 3) to assess prostate cancer patients.

This document also provides methods and materials to assist medical or research professionals in determining, at the time of PSA reoccurrence or at the time of retropubic radial prostatectomy, whether or not a mammal will later develop systemic disease or in determining, at the time of systemic disease, whether or not a mammal will later die of prostate cancer. Medical professionals can be, for example, doctors, nurses, medical laboratory technologists, and pharmacists. Research professionals can be, for example, principle investigators, research technicians, postdoctoral trainees, and graduate students. A professional can be assisted by (1) determining the level of one or more than one biomarker in a sample, and (2) communicating information about that level to that professional.

Any method can be used to communicate information to another person (e.g., a professional). For example, information can be given directly or indirectly to a professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

The invention will be further described in the following examples, which do not limit the scope of the invention described in the claims.

EXAMPLES

Example 1

A Tissue Biomarker Panel that Predicts which Men with a Rising PSA Post-Definitive Prostate Cancer Therapy Will have Systemic Progression After therapy for prostate cancer many men develop a rising PSA. Such men may develop a local or metastatic recurrence that warrants further therapy. However many men will have no evidence of disease progression other than the rising PSA and will have a good outcome. A case-control design, incorporating test and validation cohorts, was used to test the association of gene expression results with outcome after PSA progression. Using arrays optimized for paraffin-embedded tissue RNAs, a gene expression model significantly associated with systemic progression after PSA progression was developed. The model also predicted prostate cancer death (in men with systemic progression) and systemic progression beyond 5 years (in PSA controls) with hazard ratios 2.5 and 4.7, respectively (log-rank p-values of 0.0007 and 0.0005). The measurement of gene expression pattern may be useful for determining which men may benefit from additional therapy after PSA recurrence.

Gene Selection and Array Design for the DASL™ Assay:

Two Illumina DASL expression microarrays were utilized for the experiments: (1) The standard commercially available Illumina DASL expression microarray (Cancer Panel™ v1) containing 502 oncogenes, tumor suppressor genes and genes in their associated pathways. Seventy-eight of the targets on the commercial array have been associated with prostate cancer progression. (2) A custom Illumina DASL™ expression microarray containing 526 gene targets for RNAs, including genes whose expression is altered in association with prostate cancer progression. Four different sets of prostate cancer aggressiveness genes were included in the study. If the genes were not present on the Cancer Panel v1 array, then they were included in the design of the custom array:

1) Markers of prostate cancer aggressiveness identified by a Mayo/University of Minnesota Partnership (Kube et al., BMC Mol. Biol., 8:25 (2007)): The expression profiles of 100 laser-capture microdissected prostate cancer lesions and matched normal and BPH control lesions were analyzed using Affymetrix HG-U133 Plus 2.0 microarrays. Ranked lists of significantly over- and under-expressed genes comparing 10 Gleason 5 and 7 metastatic lesions to 31 Gleason 3 cancer lesions were generated. The top 500 genes on this list were compared to lists generated from prior expression microarray studies and other marker studies of prostate cancer (see 2-4 next). After this analysis there was space for 204 novel targets with potential association with aggressive prostate cancer on the custom array.

2) Markers associated with prostate cancer aggressiveness from publicly available expression microarray datasets (e.g. EZH2, AMACR, hepsin, PRLz, PRL3): Sufficiently large datasets from 9 prior microarray studies of prostate cancer of varying grades and metastatic potential (Dhanasekaran et al., Nature. 412, 822-826 (2001); Luo et al., Cancer Res. 61, 4683-4688 (2001); Magee et al., Cancer Res. 61, 5692-5696 (2001); Welsh et al., Cancer Res. 61, 5974-5978 (2001); LaTulippe et al., Cancer Res. 62, 4499-4506 (2002), Singh et al., Cancer Cell. 1, 203-209 (2002); Olinsky et al., J Clin Invest. 113, 913-923 (2004); Lapointe et al., Proc Natl Acad Sci US A. 101, 811-816 (2004); and Yu et al., J Clin Oncol. 22, 2790-2799 (2004)) were available from the OncoMine internet site (Rhodes et al., Neoplasia. 6, 1-6 (2004); Rhodes et al., Proc Natl Acad Sci US A. 101, 9309-9314 (2004); www.oncomine.org) when the array was designed. From ordered lists of these data, 32 genes were selected for inclusion on the array.

3) Previously published markers associated with prostate cancer aggressiveness (e.g. PSMA, PSCA, Cav-1): Expression microarray data has also been published. This literature was evaluated for additional tissue biomarkers. For example, at the time of array design 13 high quality expression microarray studies of prostate cancer aggressiveness were identified (See Supplemental Tables 1 and 2 of U.S. Provisional Patent Application No. 61/057,698, filed May 30, 2008, for full reference list). In addition, among the 13 reports, 5 papers presented 8 expression biomarker panels to predict prostate cancer aggressiveness (Singh et al., Cancer Cell. 1, 203-209 (2002); Glinsky et al., J Clin Invest. 113, 913-923 (2004); Lapointe et al., Proc Natl Acad Sci USA. 101, 811-816 (2004); Yu et al., J Clin Oncol. 22, 2790-2799 (2004); and Glinsky et al., J Clin Invest. 115, 1503-1521 (2005)). When appropriate probes suitable for the DASL chemistry could be designed for these panels they were included on the custom array. 12 articles were identified reviewing genes associated with prostate cancer. These criteria resulted in the selection of 150 genes.

4) Markers derived from Mayo SPORE research (including genes and ESTs mapped to 8q24). Ninety-three additional biomarkers were identified (see Supplemental Tables 1 and 2 of U.S. Provisional Patent Application No. 61/057, 698, filed May 30, 2008).

The custom array also included probe sets for 47 genes that were not expected to differ between case and control groups. Thirty-eight of these genes were also present on the commercial array (see Supplemental Tables 1 and 2 of U.S. Provisional Patent Application No. 61/057,698, filed May 30, 2008).

After enumerating the potentially prostate cancer relevant genes on the commercially available cancer panel, 557 potentially prostate cancer relevant genes and 424 other cancer-related genes were evaluated across both arrays.

Design of Nested Case-Control Study:

Since training and validation analysis requires tissue from patients with sufficient follow-up time, for this study individuals from the Mayo Radical Retropubic Prostatectomy (RRP) Registry were sampled. The registry consists of a population of men who received prostatectomy as their first treatment for prostate cancer at the Mayo Clinic (For a current description and use of the registry; see Tollefson et al., Mayo Clin Proc. 82, 422-427 (2007)). As systemic progression is relatively infrequent, a case-control study nested within a cohort of men with a rising PSA was designed. Between 1987-2001, inclusive, 9,989 previously-untreated men had RRP at Mayo. On follow-up, 2,131 developed a rising PSA (>30 days after RRP) in the absence of concurrent clinical recurrence. PSA rise was defined as a follow-up PSA>=0.20 ng/ml, with the next PSA at least 0.05 ng/ml higher or the initiation of treatment for PSA recurrence (for patients whose follow-up PSA was high enough to warrant treatment). This group of 2,131 men comprises the underlying cohort from which SYS cases and PSA controls were selected.

Within 5 years of PSA rise, 213 men developed systemic progression (SYS cases), defined as a positive bone scan or CT scan. Of these, 100 men succumbed to a prostate cancer-specific death, 37 died from other causes, and 76 remain at risk.

PSA progression controls (213) were selected from those men without systemic progression within 5 years after the PSA rise and were matched (1:1) on birth year, calendar year of PSA rise and initial diagnostic pathologic Gleason score (<=6, 7+). Twenty of these men developed systemic progression greater than 5 years after initial PSA rise and 9 succumbed to a prostate cancer-specific death.

A set of 213 No Evidence of Disease (NED) Progression controls were also selected from the Mayo RRP Registry of 9,989 men and used for some comparisons. These controls had RRP from 1987-1998 with no evidence of PSA rise within 7 years of RRP. The median (25th, 75th percentile)

follow-up from RRP was 11.3 (9.3, 13.8) years. The NED controls were matched to the systemic progression cases on birth-year, calendar year of RRP and initial diagnostic Gleason Score. Computerized optimal matching was performed to minimize the total "distance" between cases and controls in terms of the sum of the absolute difference in the matching factors (Bergstralh et al., Epidemiology. 6, 271-275 (1995)).

Block Identification, RNA Isolation, and Expression Analysis:

The list of 639 cases and controls was randomized. An attempt was made to identify all available blocks from the RRP (including apparently normal and abnormal lymph nodes) from the randomized list of 639 eligible cases and controls. Maintaining the randomization, each available block was assessed for tissue content by pathology review, and the block containing the dominant Gleason pattern cancer was selected for RNA isolation.

Four freshly cut 10 μm sections of FFPE tissue were deparaffinized and the Gleason dominant cancer focus was macrodissected. RNA was extracted using the High Pure RNA Paraffin Kit from Roche (Indianapolis, Ind.). RNA was quantified using ND-1000 spectrophotometer from Nano-Drop Technologies (Wilmington, Del.). The RNAs were distributed on 96-well plates in the randomized order for DASL analysis (including within-run and between-run duplicates).

Probes for the custom DASL® panel were designed and synthesized by Illumina, Inc. (San Diego, Calif.). RNA samples were processed in following the manufacturer's manual. Samples were hybridized to Sentrix Universal 96-Arrays and scanned using Illumina's BeadArray Reader.

In order to evaluate the accuracy of the gene expression levels defined by the DASL technology, quantitative SYBR Green RT-PCR reactions were performed for 9 selected "target" genes (CDH1, MUC1, VEGF, IGFBP3, ERG, TPD52, YWHAZ, FAM13C1, and PAGE4) and four commonly-used endogenous control genes (GAPDH, B2M, PPIA and RPL13a) in 384-well plates, with the use of Prism 7900HT instruments (Applied Biosystems, Foster City, Calif.). 210 RNA samples with abundant mRNA from the group of total 639 patients were analyzed. For the PAGE4 assay, only 77 samples were subjected to the assay because of mRNA shortage. mRNA was reverse-transcriptized with SuperScript III First Strand Synthesis SuperMix (Invitrogen, Carlsbad, Calif.) for first strand synthesis using random hexamer. Expression of each gene was measured (the number of cycles required to achieve a threshold, or Ct) in triplicate and then normalized relative to the set of four reference genes.

Pathology Review:

The Gleason score in the Mayo Clinic RRP Registry was the initial diagnostic Gleason score. Since there have been changes in pathologic interpretation of the Gleason Score over time, a single pathologist (JCC) reviewed the Gleason score of each of the blocks selected for expression analysis. This clinical variable was designated as the revised Gleason Score.

Statistical Methodology:

Collection of gene expression data was attempted for the 623 patients as described herein. Of these, there were 596 (nSYS=200, nPSA=201, nNED=195) patients for whom data was collected, the rest having failed one or both expression panels as described herein. To assure selection of similar training and validation sets, 100 case-control-control cohorts comprised of 133 randomly chosen SYS patients (two-thirds of 200 for training) along with their matched PSA and NED controls were selected as a proposed training set. The remaining cases and controls were treated as a proposed validation set. The clinical variables were tested for independence between the proposed training and validation sets separately within the SYS cases and the PSA controls. Discrete clinical factors (pathologic stage, hormonal treatment adjuvant to RRP, radiation treatment adjuvant to RRP, hormonal treatment adjuvant to PSA recurrence, and radiation therapy adjuvant to PSA recurrence) were tested using Chi-square analysis. Continuous clinical variables (Gleason score (revised), age at PSA recurrence, first rising PSA value, second rising PSA value, and PSA slope) were tested using Wilcoxon rank sum. Six of the one hundred randomly sampled sets failed to show dependency for any of the clinical variables at the 0.2 level, and the first of these was chosen as the training set: 391 patients (nSYS=133, nPSA=133, nNED=125). This reserved 205 patients for the validation set (nSYS=67, nPSA=68, nNED=70).

The purpose of array normalization is to remove systemic biases introduced during the sample preparation, hybridization, and scanning process. Since different samples were randomly assigned to arrays and positions on arrays, the data was normalized by total fluorescence separately within each disease group within each array type. The normalization technique used was fast cyclic loess (fastlo) (Ballman et al., Bioinformatics. 20, 2778-2786 (2004)).

The training data were analyzed using random forests (Breiman, Machine Learning. 45, 5-32 (2001)) using R Version 2.3.1 (www.r-project.org) and randomForest version 4.5-16 (stat-www.berkeley.edu/users/breiman/RandomForests). The data were analyzed by panel (Cancer, Custom and Merged, where Merged was the Cancer and Custom data treated as a single array). By testing the ntree parameter of the randomForest function, it was determined that 4000 random forests were sufficient to generate a stable list of markers. The top markers as sorted for significance by the randomForest program were combined with various combinations of clinical variables using logistic regression R program (glm( ) with family=binary (a logistic model), where glm refers to generalized linear model). The resulting scoring function was then analyzed using Receiver Operating Characteristic (ROC) methods, and the cut-off was chosen that assumed an equal penalty for false positives and false negatives. A review of the models permitted a subset of markers to be identified, and a subset of supporting clinical data identified. The number of features in the model was determined by leave ⅓ out Monte Carlo Cross Validation (MCCV) using 100 iterations. The number of features was selected to maximize AUC and minimize random variation in the model. The final model was then applied to the 391 patient training set and the reserved 205 patient validation set. For comparison, other previously reported gene expression models were also tested against the training and validation sets (Singh et al., Cancer Cell. 1, 203-209 (2002); Glinsky et al., J Clin Invest. 113, 913-923 (2004); Lapointe et al., Proc Natl Acad Sci US A. 101, 811-816 (2004); Yu et al., J Clin Oncal. 22, 2790-2799 (2004); and Glinsky et al., J Clin Invest. 115, 1503-1521 (2005)).

Study Design/Paraffin Block Recovery/RNA Isolation and Expression Panel Success

Figure 5:
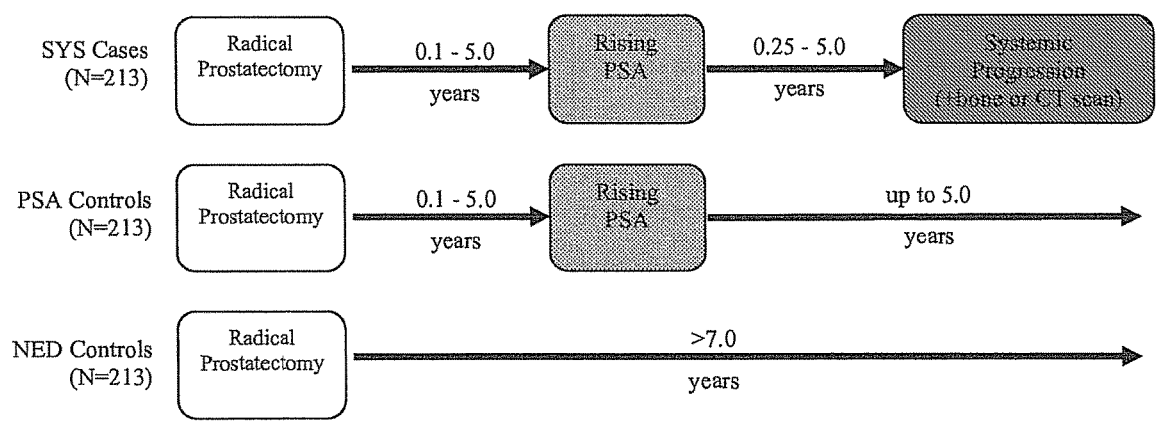
FIG. 5 is a summary of the nested case-control study design.

Briefly, a nested case-control study was performed using the large, well-defined cohort of men with rising PSA following radical prostatectomy at our institution. FIG. 5 summarizes the study design. SYS cases were 213 men who developed systemic progression between 90 days and 5.0 years following the PSA rise. PSA control were a random sample of 213 men post-radical prostatectomy with PSA recurrence with no evidence of further clinical progression within 5 years. NED controls were a random sample of 213 men post-radical prostatectomy without PSA rise within 7 years (the comparison of PSA controls with NED controls—to assess markers of PSA recurrence—will be presented in a subsequent paper). SYS cases and PSA controls were matched (1:1) on birth year, calendar year of PSA rise, initial diagnostic pathologic Gleason score (<=6 vs. >=7). The list of eligible cases and controls was scrambled for the blind ascertainment of blocks, isolation of RNA and performance of the expression array experiments.

Table 1A summarizes the distribution of clinical parameters between the SYS cases and the PSA and NED control groups. As expected, there was no significant difference between the groups for the variables used for matching (there was no significant difference in Gleason score when the <=6 and >7 groups—the matching criteria—were compared). Because Gleason scoring may have changed over time, all of the macrodissected lesions were blindly re-graded by a single experienced pathologist (providing a revised Gleason score). As expected, Gleason scores have increased over time. In addition, the proportion of Gleason 8-10 tumors increased comparing NED controls to PSA controls, and PSA controls to SYS cases. Because of this change in grade, the revised Gleason score was used in all the biomarker modeling.

All paraffin-embedded blocks from eligible men were identified, and each block was surveyed for the tissue present (primary and secondary Gleason cancer regions, normal and metastatic lymph nodes, etc.). The dominant Gleason pattern region was macrodissected from the available blocks, and RNA was isolated from that region. Illumina Cancer Panel™ and custom prostate cancer panel DASL array analyses were then performed on all RNA specimens. The Experimental Procedures section and Supplemental Tables 1 & 2 of U.S. Provisional Patent Application No. 61/057,698, filed May 30, 2008, describe the composition of the Cancer Panel and the design of the Custom Panel.

Table 1B summarizes the final block availability, the RNA isolation success rate, and the success rates of the expression array analyses. Of the 639 eligible patients, paraffin blocks were available on 623 (97.5%). Similarly, RNA was successfully isolated and the DASL assays successfully performed on a very high proportion of patients/specimens: Usable RNA was prepared from all 623 blocks, and the Cancer Panel and custom prostate cancer panel DASL arrays were both successful (after repeating some specimens—see below) on 596 RNA specimens (95.7% of RNAs; 93.3% of design patients). Only 9 (1.4%) RNA specimens failed both expression panels. The primary reason for these failures was poor RNA quality—as measured by qRT-PCR of the RPL13A gene expression (Bibikova et al., *Genomics*, 89(6):

TABLE 1A

Systemic progression (SYS) Case and PSA recurrence (PSA) and no evidence of disease (NED) control patient demographics

| | Progression group | | | p-value | |
|---|---|---|---|---|---|
| | NED controls | PSA controls | SYS cases | NED vs. PSA | PSA vs. SYS |
| Year of surgery | | | | 0.707 | 0.592 |
| N | 213 | 213 | 213 | | |
| Median | 1992 | 1992 | 1992 | | |
| Q1, Q3 | 1989, 1995 | 1990, 1995 | 1989, 1995 | | |
| Age at RRP | | | | 0.682 | 0.496 |
| N | 213 | 213 | 213 | | |
| Median | 67 | 67 | 67 | | |
| Q1, Q3 | 61, 70 | 61, 70 | 61, 70 | | |
| PSA at RRP | | | | 0.001 | 0.957 |
| N | 205 | 208 | 204 | | |
| Median | 8.1 | 10.5 | 10.6 | | |
| Q1, Q3 | 5.1, 13.1 | 6.4, 21.4 | 6.5, 20.7 | | |
| Gleason score, original | | | | 0.411 | 0.024 |
| Missing | 12 | 6 | 14 | | |
| <=6 | 45 (22.4%) | 48 (23.2%) | 46 (23.1%) | | |
| 7 | 139 (69.2%) | 129 (62.3%) | 94 (47.2%) | | |
| 8-10 | 17 (8.5%) | 30 (14.5%) | 59 (29.6%) | | |
| Gleason score, revised | | | | 0.002 | <0.001 |
| Missing | 8 | 2 | 6 | | |
| <=6 | 50 (22.4%) | 32 (15.2%) | 8 (3.9%) | | |
| 7 | 114 (55.6%) | 113 (53.6%) | 75 (36.2%) | | |
| 8-10 | 41 (20.0%) | 66 (31.3%) | 124 (59.9%) | | |
| Stage | | | | 0.138 | <0.001 |
| T2N0 | 118 (55.4%) | 95 (44.6%) | 59 (27.7%) | | |
| T3aN0 | 43 (20.2%) | 53 (24.9%) | 47 (22.1%) | | |
| T3bN0 | 21 (9.9%) | 54 (25.4%) | 56 (26.3%) | | |
| T3xN+ | 31 (14.6%) | 11 (5.2%) | 51 (23.9%) | | |
| Ploidy | | | | 0.525 | 0.001 |
| Missing | 13 | 9 | 1 | | |
| Diploid | 136 (68.0%) | 128 (62.7%) | 97 (45.8%) | | |
| Tetraploid | 53 (26.5%) | 61 (29.9%) | 84 (39.6%) | | |
| Aneuploid | 11 (5.5%) | 15 (7.4%) | 31 (14.6%) | | |
| Age at PSA recurrence | | | | NA | 0.558 |
| N | | 213 | 213 | | |
| Median | | 69.1 | 69.6 | | |
| Q1, Q3 | | 64.2, 73.4 | 64.7, 73.8 | | |

666-72 (2007)). Of the 1246 initial samples run on both panels, 87 (7.0%) specimens failed. Those specimens for which there was residual RNA were repeated with a success rate of 77.2% (61 of 79 samples).

TABLE 1B

Availability of blocks, RNA isolation success and DASL assay success

|  | Pregression Case/ Control Group | | | |
| --- | --- | --- | --- | --- |
|  | None | PSA | Systemic | Total |
| Design Number | 213 | 213 | 213 | 639 |
| Blocks Available | 205 | 211 | 207 | 623 (97.5%) |
| Usable RNA | 205 | 211 | 207 | 623 |
| Evaluable Data, Both DASL Panels | 195 | 201 | 200 | 596 (95.7%) |
| Evaluable Data, Cancer Panel | 3 | 5 | 2 | 10 |
| Evaluable Data, Custom Panel | 2 | 3 | 3 | 8 |
| Failed Both Panels | 5 | 2 | 2 | 9 (1.4%) |

Expression Analysis Reproducibility

Replicate analysis results, RT-PCR comparisons, and inter- and intra-panel gene expression comparisons are as follows.

Figure 6:
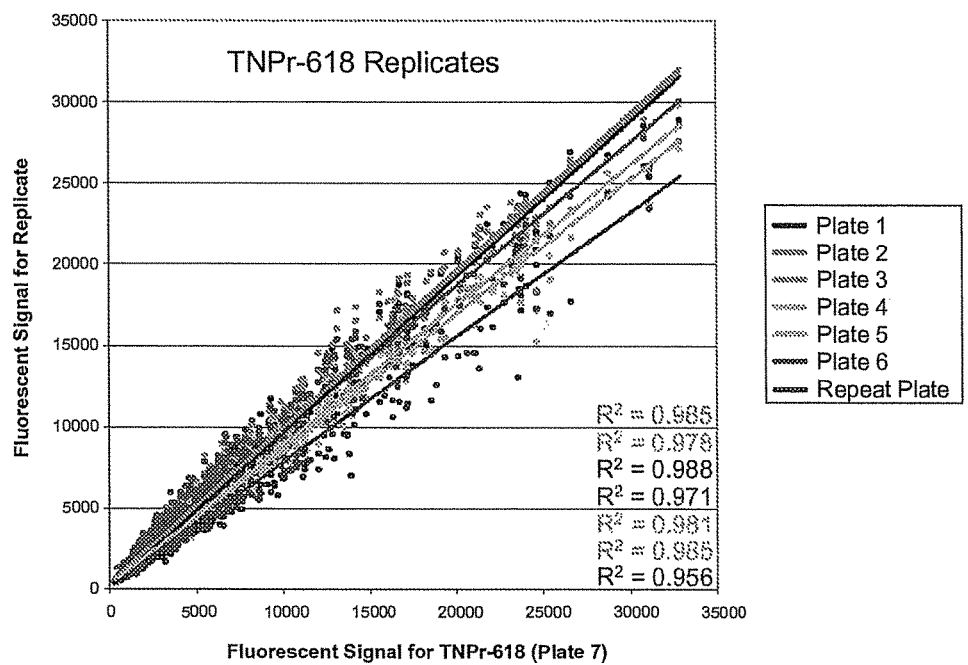
FIG. 6: Reproducibility of DASL assay and the effect of RNA quantity on the DASL assay. (A) An example of DASL interplate reproducibility. (B) Effect of reduced RNA quantity on the DASL assay.
Figure 6:
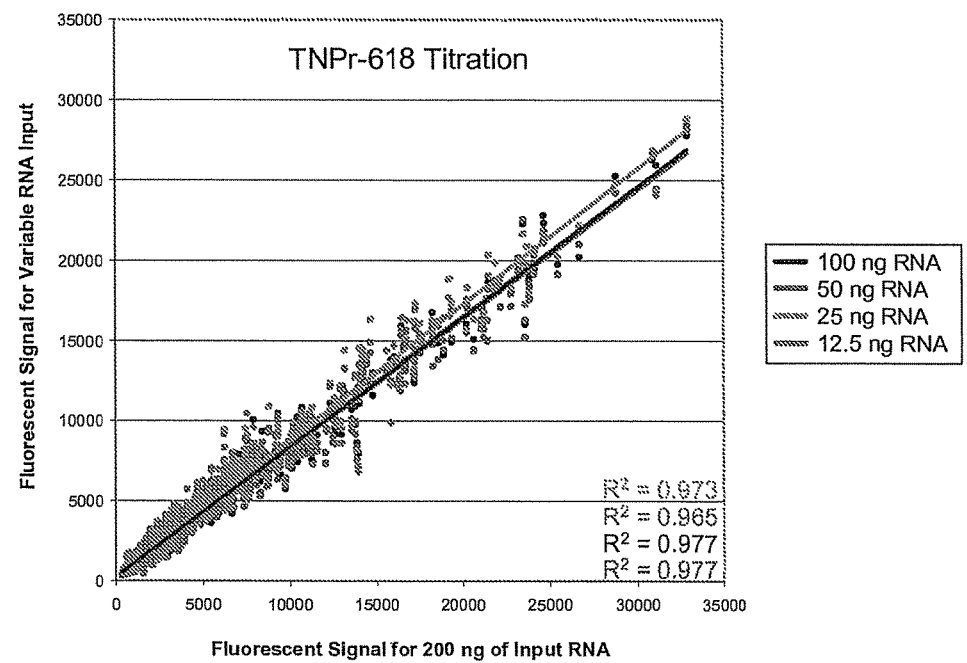

Replicate analyses: The study design included several intra- and inter-run array replicates. To determine inter-run array variability, two specimens were run on each of 8 Cancer Panel v1 array runs. The median (range) inter-run correlation coefficients (r2) comparing these two specimen replicates were 0.94 (0.89-0.95) and 0.98 (0.90-0.98), respectively. The same two specimens were run on each of 8 custom prostate cancer panel array runs. The median (range) inter-run correlation coefficients (r2) comparing these specimen replicates were 0.97 (0.95-0.98) and 0.98 (0.96-0.99), respectively. FIG. 6A summarizes the inter-run replicates for one of the specimens on the custom panel. Twelve specimens were evaluated as intra-run array replicates. The median (range) intra-run r2 values comparing these paired specimens on the Cancer Panel v1 was 0.98 (0.93-0.99). The median (range) intra-run r2 values comparing these paired specimens on the custom panel was 0.98 (0.88-0.99). Two specimens were serially diluted, and the expression results of the diluted RNA specimens compared to that of the standard 200 ng of the parental RNA specimen. The r2 for RNA specimens of 25, 50, and 100 ng ranged from 0.98-0.99 (FIG. 6B) with slopes near 1.0.

Figure 7:
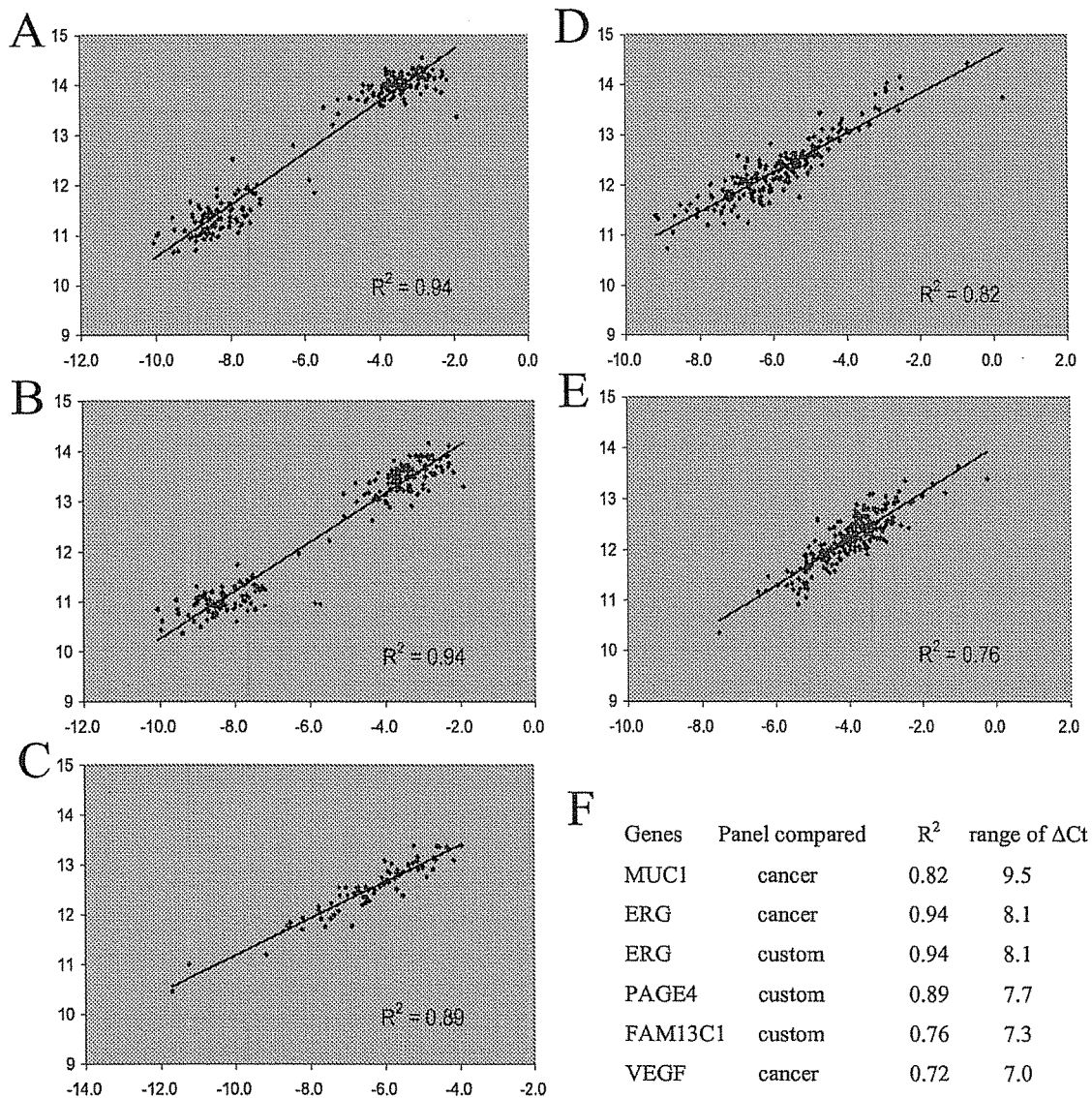
FIG. 7: (A to E) Example results of the comparison of quantitative RT-PCR and DASL data on ERG—Cancer Panel ver1 (A, $R2=0.94$), ERG—Custom Panel (B, $R2=0.94$), PAGE4 (C, $R2=0.89$), MUC1 (D, $R2=0.82$), and FAM13C1 (E, $R2=0.75$). (F) Summary of quantitative RT-PCR and DASL data comparisons.

Comparison with RT-PCR: RT-PCR analyses were performed for 9 genes (CDH1, VEGF, MUC1, IGFBP3, ERG, TPD52, YWHAZ, FAM13C1, and PAGE4) on 210 samples. Example results are illustrated in FIG. 7. Comparison of the quantitative RT-PCR and the DASL results gave r2 values of 0.72-0.94 for genes with dynamic range of at least 7 $\Delta$CTs. Genes with a smaller dynamic range of $\Delta$CT gave r2 values of 0.15-0.79 (FIG. 7). Thus, both the DASL and RT-PCR measurements appear to be highly correlated with each other when there is a broad range of RNA expression values.

Figure 8:
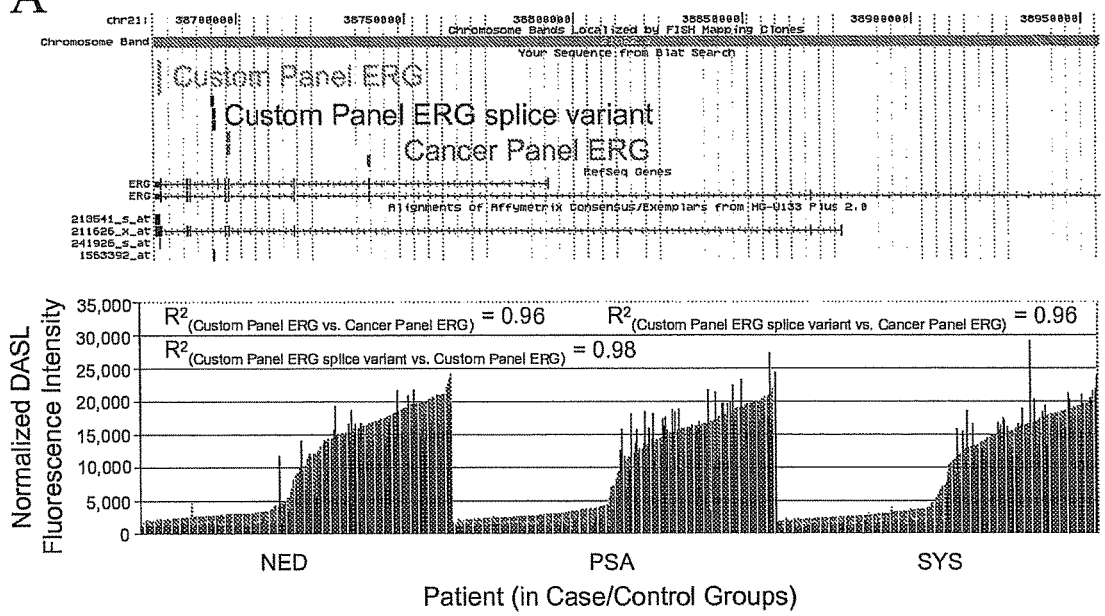
FIG. 8: Comparison of genes having multiple probe sets on the Cancer Panel v1 and/or the Custom panel. (A) Comparison of three probe sets (Cancer Panel ERG, Custom Panel ERG and Custom panel ERG splice variant) for ERG. (B) Comparison of two probe sets (Custom Panel SRD5A2 and Custom panel terparbo) for SRD5A2/terparbo.
Figure 8:
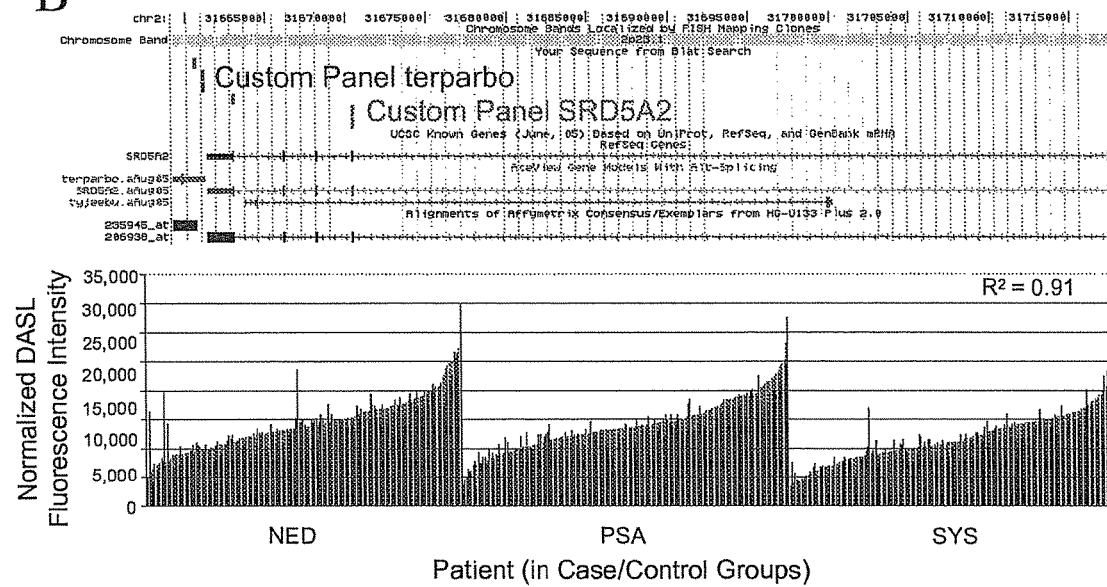

Inter- and Intra-Panel Gene Expression Comparisons: By design several genes were evaluated twice on the custom and/or cancer panels. As an example of a specific inter-panel gene expression comparison, probe sets for ERG were present on both the custom (two 3 probe sets) and cancer (one 3 probe set) panels. The r2 comparing the 2 custom probe sets with the commercial probe set for all 596 patients was 0.96 in both cases (FIG. 8A). As an example of a specific intra-custom panel gene expression comparison are the probe sets for SRD5A2 and terparbo. Terparbo is a "novel" gene which is likely a variant of the SRD5A2 transcript (UCSC browser, genome.ucsc.edu). The r2 comparing the two custom probe sets for SRD5A2 and terparbo was 0.91 (FIG. 8B).

Specific Gene Expression Results Comparing the Systemic Progression Cohorts with the PSA Progression and No Evidence of Progression Cohorts:

Univariate Analyses by gene: Because the DASL assay appeared to generate precise and reproducible results, the array data was examined for genes whose expression was significantly altered when the SYS cases were compared with the PSA Controls. For this initial analysis, the DASL gene expression value was determined to be the average of the up-to-three probes for each gene on each array. Upon univariate analysis (two-sided t-test) of the probe-averaged and total fluorescence fast-lo normalized data, 68 genes were highly significantly over- or under-expressed in the SYS cases versus PSA controls ($p<9.73\times10^{-7}$, Bonferroni correction for $p<0.001$) (Table 2). One hundred twenty-six genes were significantly over- or under-expressed in the SYS cases versus the PSA controls ($p<4.86\times10^5$, Bonferroni correction for $p<0.05$). Supplemental Table 3 of U.S. Provisional Patent Application No. 61/057,698, filed May 30, 2008, provides the complete gene list ordered by p-value. FIG. 1 illustrates nine genes with significantly different expression in the SYS cases and PSA controls.

TABLE 2

Top 68 genes highly significantly correlated with prostate cancer systemic progression ($p < 0.001$; with Bonferroni correction $p < 9.73E–07$).

| | | | DASL fast-lo Normalized Expression Value | | Systemic | Systemic |
| --- | --- | --- | --- | --- | --- | --- |
| Rank | Gene Name | Gene ID* | Systemic Progression | PSA Progression | to PSA Fold change | to PSA p-value** |
| 1 | RAD21*** | NM_006265 | 7587 | 6409 | 1.18 | 8.57E–14 |
| 2 | YWHAZ | NM_145690 | 15625 | 13417 | 1.16 | 1.92E–13 |
| 3 | TAF2*** | NM_003184 | 3144 | 2681 | 1.17 | 6.99E–13 |
| 4 | SLC44A1 | NM_080546 | 4669 | 4022 | 1.16 | 2.74E–12 |
| 5 | IGFBP3 | NM_000598 | 4815 | 3782 | 1.27 | 3.75E–12 |
| 6 | RHOA | NM_001664 | 15859 | 14542 | 1.09 | 1.22E–11 |
| 7 | MTPN | NM_145808 | 7646 | 6840 | 1.12 | 1.69E–11 |
| 8 | BUB1 | NM_001211 | 1257 | 957 | 1.31 | 2.07E–11 |

TABLE 2-continued

Top 68 genes highly significantly correlated with prostate cancer systemic progression (p < 0.001; with Bonferroni correction p < 9.73E–07).

| Rank | Gene Name | Gene ID* | DASL fast-lo Normalized Expression Value | | Systemic to PSA Fold change | Systemic to PSA p-value** |
|---|---|---|---|---|---|---|
| | | | Systemic Progression | PSA Progression | | |
| 9 | TUBB | NM_178014 | 17412 | 15659 | 1.11 | 6.52E−11 |
| 10 | CHRAC1*** | NM_017444 | 3905 | 3233 | 1.21 | 6.74E−11 |
| 11 | HPRT1 | NM_000194 | 3613 | 3179 | 1.14 | 8.19E−11 |
| 12 | SEC14L1 | NM_003003 | 7248 | 6185 | 1.17 | 8.20E−11 |
| 13 | SOD1 | NM_000454 | 17412 | 16043 | 1.09 | 1.30E−10 |
| 14 | ENY2 | NM_020189 | 7597 | 6493 | 1.17 | 2.04E−10 |
| 15 | CCNB1 | NM_031966 | 1871 | 1342 | 1.39 | 3.65E−10 |
| 16 | INHBA | NM_002192 | 4859 | 3732 | 1.30 | 5.18E−10 |
| 17 | TOP2A | NM_001067 | 5550 | 4123 | 1.35 | 7.42E−10 |
| 18 | ATP5J | NM_001003703 | 13145 | 11517 | 1.14 | 1.75E−09 |
| 19 | C8orf53*** | NM_032334 | 7373 | 6444 | 1.14 | 1.88E−09 |
| 20 | EIF3S3*** | NM_003756 | 11946 | 10798 | 1.11 | 1.98E−09 |
| 21 | EIF2C2*** | NM_012154 | 5908 | 5338 | 1.11 | 2.12E−09 |
| 22 | CDKN3 | NM_005192 | 1562 | 1229 | 1.27 | 2.32E−09 |
| 23 | TPX2 | NM_012112 | 1193 | 861 | 1.39 | 2.64E−09 |
| 24 | GLRX2 | NM_197962 | 4154 | 3319 | 1.25 | 3.13E−09 |
| 25 | CTHRC1 | NM_138455 | 3136 | 2480 | 1.26 | 3.83E−09 |
| 26 | KIAA0196*** | NM_014846 | 5530 | 4945 | 1.12 | 4.12E−09 |
| 27 | DHX9 | NM_030588 | 7067 | 6607 | 1.07 | 5.02E−09 |
| 28 | FAM13C1 | NM_001001971 | 4448 | 5416 | 0.82 | 9.07E−09 |
| 29 | CSTB | NM_000100 | 16424 | 15379 | 1.07 | 1.57E−08 |
| 30 | SESN3.a | SESN3.a | 8467 | 6811 | 1.24 | 1.99E−08 |
| 31 | SQLE*** | NM_003129 | 2282 | 1832 | 1.25 | 2.43E−08 |
| 32 | IMMT | NM_006839 | 4683 | 4190 | 1.12 | 2.43E−08 |
| 33 | MKI67 | NM_002417 | 4204 | 3261 | 1.29 | 2.91E−08 |
| 34 | MRPL13*** | NM_014078 | 5051 | 4158 | 1.21 | 3.80E−08 |
| 35 | SRD5A2 | NM_000348 | 2318 | 2795 | 0.83 | 4.63E−08 |
| 36 | EZH2 | NM_004456 | 3806 | 3257 | 1.17 | 4.76E−08 |
| 37 | F2R | NM_001992 | 3856 | 3203 | 1.20 | 5.61E−08 |
| 38 | SH3KF2.a | SH3RF2.a | 1394 | 1705 | 0.82 | 6.48E−08 |
| 39 | ZNF313 | NM_018683 | 9542 | 8766 | 1.09 | 7.14E−08 |
| 40 | SDHC | NM_001035511 | 2363 | 2082 | 1.14 | 7.35E−08 |
| 41 | PGK1 | NM_000291 | 2313 | 2001 | 1.16 | 7.84E−08 |
| 42 | GNPTAB | NM_024312 | 5427 | 4587 | 1.18 | 9.04E−08 |
| 43 | meelar.d | meelar.d | 2566 | 3478 | 0.74 | 9.59E−08 |
| 44 | THBS2 | NM_003247 | 3047 | 2458 | 1.24 | 9.72E−08 |
| 45 | BIRC5 | NM_001168 | 2451 | 1802 | 1.36 | 1.00E−07 |
| 46 | POSTN | NM_006475 | 7210 | 5812 | 1.24 | 1.02E−07 |
| 47 | GNB1 | NM_002074 | 12350 | 11206 | 1.10 | 1.20E−07 |
| 48 | FAM49B*** | NM_016623 | 6291 | 5661 | 1.11 | 1.21E−07 |
| 49 | WDR67*** | NM_145647 | 1655 | 1423 | 1.16 | 1.67E−07 |
| 50 | TMEM65.a*** | TMEM65.a | 4117 | 3540 | 1.16 | 1.96E−07 |
| 51 | GMNN | NM_015895 | 7458 | 5945 | 1.25 | 1.99E−07 |
| 52 | PAGE4 | NM_007003 | 6419 | 8065 | 0.80 | 2.00E−07 |
| 53 | MYBPC1 | NM_206821 | 8768 | 11120 | 0.79 | 2.61E−07 |
| 54 | GPR137B | NM_003272 | 3997 | 3447 | 1.16 | 2.96E−07 |
| 55 | ALAS1 | NM_000688 | 5380 | 5035 | 1.07 | 3.55E−07 |
| 56 | MSR1 | NM_002445 | 3663 | 3025 | 1.21 | 3.65E−07 |
| 57 | CDC2 | NM_033379 | 1420 | 1130 | 1.26 | 3.90E−07 |
| 58 | 240093_x_at | 240093_x_at | 1789 | 1469 | 1.22 | 4.71E−07 |
| 59 | IGFBP3 | NM_000598 | 10673 | 9433 | 1.13 | 4.85E−07 |
| 60 | RAP2B | NM_002886 | 3270 | 2922 | 1.12 | 5.00E−07 |
| 61 | MGC14595.a*** | MGC14595.a | 2252 | 1995 | 1.13 | 5.46E−07 |
| 62 | AZGP1 | NM_001185 | 17252 | 20133 | 0.86 | 6.55E−07 |
| 63 | NOX4 | NM_016931 | 2321 | 1942 | 1.19 | 6.67E−07 |
| 64 | STIP1 | NM_006819 | 7630 | 7123 | 1.07 | 7.23E−07 |
| 65 | PTPRN2 | NM_130843 | 4471 | 5398 | 0.83 | 7.36E−07 |
| 66 | CTNNB1 | NM_001904 | 9989 | 9354 | 1.07 | 7.50E−07 |
| 67 | C8orf76*** | NM_032847 | 4088 | 3652 | 1.12 | 7.88E−07 |
| 68 | YY1 | NM_003403 | 9529 | 8635 | 1.10 | 8.08E−07 |

*The Gene ID is the accession number when available. Other Gene IDs can be found by searching the May 2004 assembly of the human genome at genome.ucsc.edu/cgi-bin/hgGateway.
**t-test
***Genes mapped to 8q24

Systemic Progression Prediction Model Development and Testing on Training Set:

The training data were analyzed by panel (cancer, custom and merged), by gene (the average expression for all gene-specific probes), and by individual probes. A statistical model to predict systemic progression (with and without clinical variables) was developed using random forests (Breiman, Machine Learning. 45, 5-32 (2001)) and logistic regression as described herein. Table 3 lists the 15 genes and 2 individual probes selected for the final model.

TABLE 3

Final random forest 17 gene/probe model to predict prostate cancer systemic progression after a rising PSA following radical prostatectomy

| | | | | Mean DASL Expression Values | | |
|---|---|---|---|---|---|---|
| t-test Rank | Symbol | Mean Gini Decrease* | p-value (t-test) | Systemic Progression | PSA Progression | Systemic:PSA Fold Change |
| 1 | RAD21** | 2.15 | 8.57E−14 | 7587 | 6409 | 1.18 |
| 22 | CDKN3 | 1.28 | 2.32E−09 | 1562 | 1229 | 1.27 |
| 15 | CCNB1 | 1.25 | 3.65E−10 | 1871 | 1342 | 1.39 |
| 12 | SEC14L1 | 1.14 | 8.20E−11 | 7248 | 6185 | 1.17 |
| 8 | BUB1 | 1.06 | 2.07E−11 | 1257 | 957 | 1.31 |
| 55 | ALAS1 | 1.04 | 3.55E−07 | 5380 | 5035 | 1.07 |
| 26 | KIAA0196** | 1.02 | 4.12E−09 | 5530 | 4945 | 1.12 |
| 3 | TAF2** | 1.02 | 6.99E−13 | 3144 | 2681 | 1.17 |
| 78 | SFRP4 | 0.99 | 1.89E−06 | 15176 | 13059 | 1.16 |
| 64 | STIP1 | 0.95 | 7.23E−07 | 7630 | 7123 | 1.07 |
| 25 | CTHRC1 | 0.90 | 3.83E−09 | 3136 | 2480 | 1.26 |
| 4 | SLC44A1 | 0.90 | 2.74E−12 | 4669 | 4022 | 1.17 |
| 5 | IGFBP3 | 0.85 | 3.75E−12 | 4815 | 3782 | 1.27 |
| 307 | EDG7 | 0.82 | 7.07E−03 | 5962 | 6757 | 0.88 |
| 48 | FAM49B** | 0.82 | 1.21E−07 | 6291 | 5661 | 1.11 |
| 19 | C8orf53** | 0.97*** | 1.88E−09 | 7373 | 6444 | 1.14 |
| 275 | CDK10 | 0.53*** | 4.12E−03 | 12254 | 12868 | 0.95 |

*Mean Gini Decrease for a variable is the average (over all random forest trees) decrease in node impurities from recursive partitioning splits on that variable. For classification, the node impurity is measured by the Gini index. The Gini index is the weighted average of the impurity in each branch, with impurity being the proportion of incorrectly classified samples in that branch. The larger the Gini decrease, the fewer the misclassification impurities.
**Genes mapped to 8q24
***Single probes for C8orf53 and CDK10 were selected. The Mean Gini Decrease for these probes are derived from an independent random forest analysis of the all probes separately.

Figure 2:
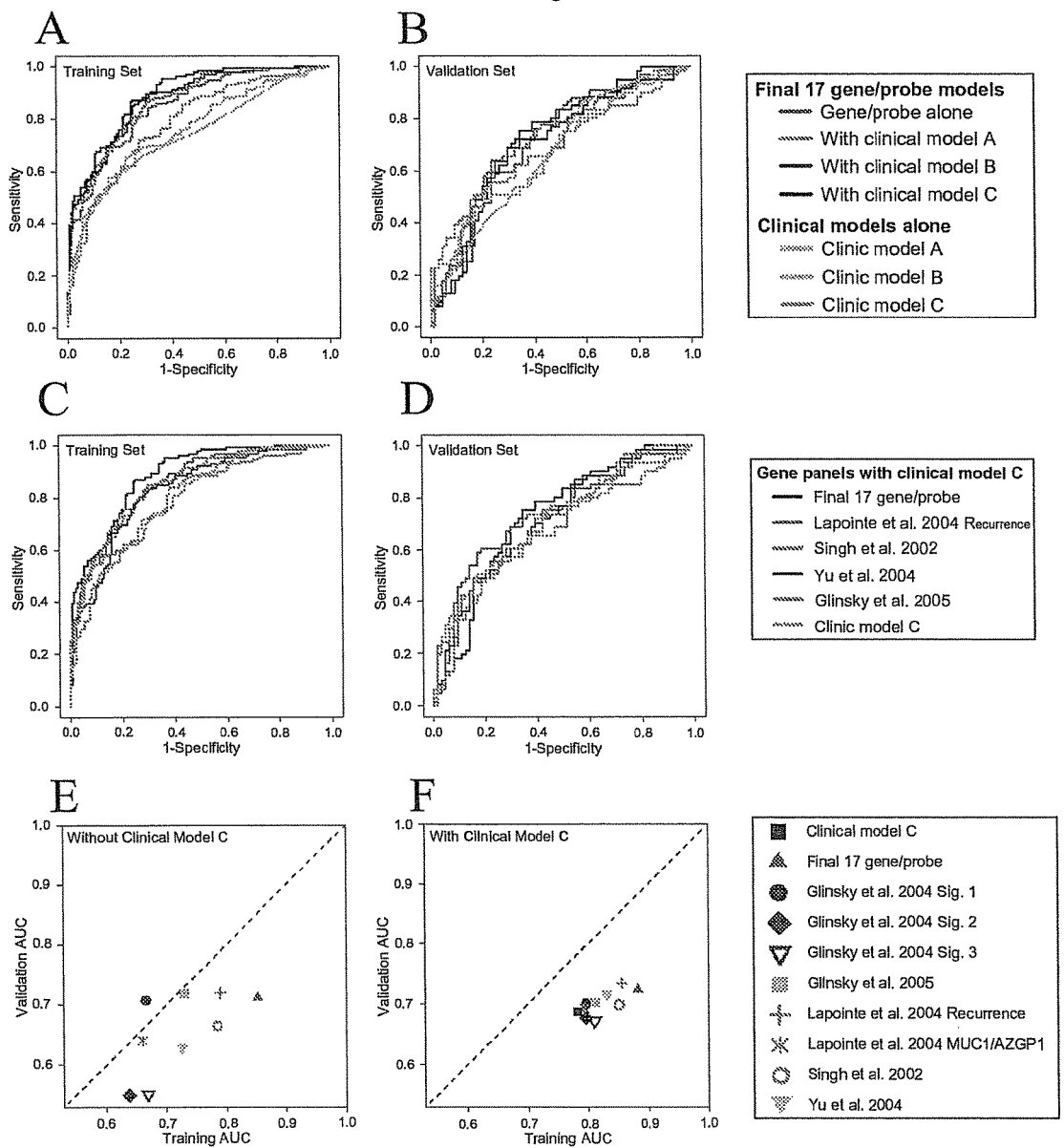
FIG. 2: (A to D) Areas under the curve (AUCs) for three clinical models, the final 17 gene/probe model and the combined clinical probe models. A. The training set AUCs for three clinical models, the final 17 gene/probe model and the combined clinical/17 gene/probe model. B. The validation set AUCs for three clinical models, the final 17 gene/probe model and the combined clinical/17 gene/probe model. C. The training set AUCs of four previously reported gene expression models of prostate cancer aggressiveness compared with the Clinical model C alone and with the 17 gene/probe model. D. The validation set AUCs of four previously reported gene expression models of prostate cancer aggressiveness compared with the clinical model C alone and with the 17 gene/probe model. For an explanation of the clinical models see Table 4. (E and F) A comparison of the training and validation set AUCs for each of the model. E. AUCs of the each of the gene/probe models alone. F. AUCs of each of the gene/probe models with the inclusion of clinical model C.

Table 4 and FIG. 2A summarize the areas under the curve (AUCs) for three clinical models, the final 17 gene/probe model and the combined clinical probe models. The variables in the clinical models were those items of clinical information that would be available at specific times in a patient's course. Clinical model A included revised Gleason score and pathologic stage—information available immediately after RRP. The addition of diagnostic PSA and age at surgery did not significantly add to the AUC and was left out of this model. Clinical model B added age at surgery, preoperative PSA value, and any adjuvant or hormonal therapy within 90 days after RRP—information available at RRP after RRP but before PSA recurrence. Clinical model C added age at PSA recurrence, the second PSA level at time of PSA recurrence, and the PSA slope—information available at the time of PSA recurrence.

TABLE 4

Prediction of systemic progression - training set AUCs

| | Probes alone | Clinical model* | | |
|---|---|---|---|---|
| | | A | B | C |
| Clinical model alone | NA | 0.736 | 0.757 | 0.783 |
| Final 17 gene/probe | 0.852 | 0.857 | 0.873 | 0.883 |
| Glinsky et al. 2004 Signature 1 | 0.665 | 0.762 | 0.776 | 0.798 |
| Glinsky et al. 2004 Signature 2 | 0.638 | 0.764 | 0.781 | 0.798 |
| Glinsky et al. 2004 Signature 3 | 0.669 | 0.770 | 0.788 | 0.810 |
| Glinsky et al. 2005 | 0.729 | 0.780 | 0.800 | 0.811 |
| Lapointe et al. 2004 Tumor Recurrence Sig. | 0.789 | 0.825 | 0.838 | 0.855 |
| Lapointe et al. 2004 (MUC1 and AZGP1) | 0.660 | 0.767 | 0.777 | 0.793 |
| Singh et al. 2002 | 0.783 | 0.824 | 0.838 | 0.851 |
| Yu et al. 2004 | 0.725 | 0.797 | 0.815 | 0.830 |

| | *Clinical model | | |
|---|---|---|---|
| Clinical variable | A | B | C |
| Revised Gleason score | X | X | X |
| pStage | X | X | X |
| Age at surgery | | X | X |
| Initial PSA at recurrence | | X | X |
| Hormone or radiation therapy after RRP | | X | X |
| Age at PSA recurrence | | | X |
| Second PSA | | | X |
| PSA slope | | | X |

A pStage or TNM staging system can be used as described elsewhere (e.g., on the World Wide Web at "upmccancer-centers.com/cancer/prostate/TNMsystem.html").

Using the training set, clinical models A, B and C alone had AUCs of 0.74 (95% CI 0.68-0.80), 0.76 (95% CI 0.70-0.82) and 0.78 (95% CI 0.73-0.84), respectively. The 17 gene/probe model alone had an AUC of 0.85 (95% CI 0.81-0.90). Together with the 17 gene/probe model, clinical models A, B, and C had AUCs of 0.86 (95% CI 0.81-0.90), 0.87 (95% CI 0.83-0.91) and 0.88 (95% CI 0.84-0.92), respectively. A 19 gene model that included the 17 gene/probe model as well as the averaged probe sets for TOP2A and survivin (BIRC5) was tested. Expression alterations have previously been reported to be associated with prostate cancer progression for both genes, and they were included in the top 68 gene list (see Table 2). The addition of these two genes did not improve the prediction of systemic progression in the training set.

The arrays were designed to contain probe sets for several previously published prostate aggressiveness models (Singh et al., 2002, Glinsky et al., 2004, Lapointe et al., 2004, Yu et al., 2004, Glinsky et al., 2005). Table 4 also summarizes the AUCs for array expression results for these models, with and without the inclusion of the three clinical models. FIG. 2C illustrates the AUCs for four of these models with the appropriate comparison with the clinical model C alone and with the 17 gene/probe model. With the clinical data, each of these models generated AUCs that were less than the developed model. However several of the models generated AUCs (e.g. Lapointe et al. 2004 recurrence model, Yu et al. 2004 model, and Singh et al. 2002 model) that were within or close to the 95% confidence limits of our AUC training set estimates.

Testing of Models on the Validation Set:

The 17 gene/probe model and the other previously published models were then applied to the reserved 205 patient validation set (FIGS. 2B and 2D). FIG. 2E compares the training and validation set AUCs of the each of the gene/probe models alone. With the exception of the Glinsky et al. 2004 Signature 1, all of the gene/probe models had significantly lower AUCs in the validation set compared to the training set. FIG. 2F compares the training and validation set AUCs of each of the gene/probe models including clinical model C. While the 17 gene/probe model and three of the previously published models (LaPointe et al. 2004 Recurrence model, Yu et al. 2004 model and Glinsky et al. 2005 model) outperformed the clinical model alone, the AUCs were significantly lower in the validation set compared to the training set.

The models were compared for their classification of patients into the known PSA progression control and SYS progression case groups. To compare models, the Cramér's V-statistic (Cramér, 1999) was used. Cramér's V-statistic measures how well two models agree. It is calculated by creating a contingency table (2×2 in this case) and computing a statistic from that table. Supplemental Table 4 of U.S. Provisional Patent Application No. 61/057,698, filed May 30, 2008, summarizes the Cramér's V-statistic of the various models, and includes a perfect predictor ("truth") model for direct evaluation of the models. Briefly, the Cramér's V-statistic ranged from 0.38 to 0.70. The lowest Cramér's V value was between the true state (perfect prediction) and the Glinsky et al. 2005 model with clinical data. The highest Cramér's V value was between our 17 gene/probe model and Singh et al. 2002 model, both with clinical data. Most of the models classified the same patients into the known groups (e.g. classifying a patient in the PSA control group as a PSA progression and a patient in the SYS case group as a systemic progression). They also tended to incorrectly classify the same patients (e.g., classifying a patient in the PSA control group as a systemic progression and vice versa). The 17 gene/probe model correctly classified 5-15 more patients into their known category (PSA controls or SYS cases) compared to the other models.

Secondary Analyses

Exploratory Survival Studies:

As noted above, the 17 gene/probe model and the previously reported models each classified some of the SYS cases in the good outcome category (e.g. to be PSA recurrences, not systemic progressors) and some of the PSA controls in the poor outcome category (e.g. to go on to systemic progression). There was a curiosity to see if these apparently false classifications had any biologic or clinical relevance.

Figure 3:
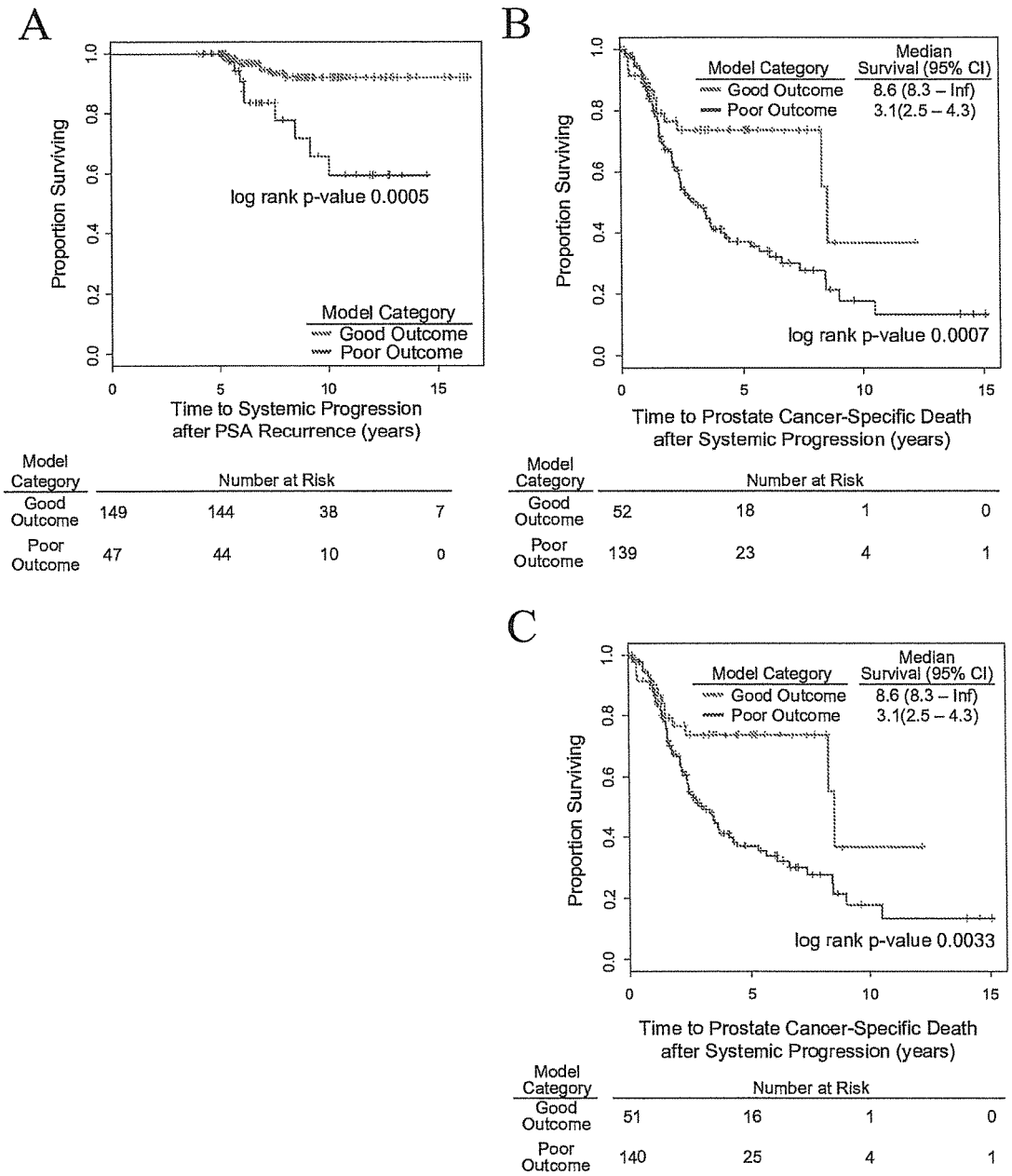
FIG. 3: Systemic progression-free and overall prostate cancer-specific survival in the PSA Control and SYS Case groups. A) Systemic progression-free survival for the patients classified in the poor outcome category and for those in the good outcome category in the PSA control group—17 gene/probe model. B) Prostate cancer-specific overall survival for the patients classified in the poor outcome category and for those in the good outcome category in the SYS case group—17 gene/probe model. C) Prostate cancer-specific overall survival for patients classified in the poor outcome category and for those in the good outcome category in the SYS case group—Lapointe et al. 2004 recurrence model.

Seventeen men in the PSA control group (who had both array and clinical model C data) went on to have systemic progression beyond 5 years at the time of last follow-up. Of these 17 patients, 9 were predicted to have a poor outcome by the 17 gene/probe model. Of the 179 patients who did not have any systemic progression, 38 were classified in the poor outcome category by the model (p value=0.0066, Fisher exact test). FIG. 3A illustrates the systemic progression-free survival for the good and poor outcome groups in the PSA controls. PSA controls whose tumor classified as having a poor outcome had significantly increased hazard of developing systemic progression beyond 5 years (log rank p-value=0.00050) (HR=4.7, 95% CI: 1.8-12.1).

Ninety-three men in the SYS case group (who also had array and clinical model C data) went on to prostate cancer death at the time of last follow-up. Of these 93 patients, 78 were predicted to have a poor outcome by the 17 gene/probe model. Of the 98 patients who did not suffer a prostate cancer death, 61 were classified in the poor outcome category by the model (p value=0.0008, chi-square test). FIG. 3B illustrates the prostate cancer-specific overall survival for the good and poor outcome groups in the SYS cases. SYS cases whose tumor classified as having a poor outcome had significantly increased hazard of suffering a prostate cancer-specific death (HR=2.5, 95% CI: 1.5-4.4). The median survival from first positive bone scan or CT was 2.8 years (95% CI: 2.4-4.2) in the group classified as having a poor outcome and 8.6 years (95% CI: 7.4-∞) in the group classified as having a good outcome (log rank p-value=0.00068).

Similar associations were observed when 3 of the previously published models with high AUCs (Lapointe et al. 2004 recurrence model and the Glinsky et al. 2005 and Yu et al. 2004 models) were evaluated. The following describes the results for the LaPointe et al. 2004 recurrence model (data for the other two models were similar and not shown). Of the 98 patients who did not suffer a prostate cancer death, 60 were predicted to have a poor outcome by the Lapointe et al. 2004 recurrence model (p value=0.0001, chi-square test). FIG. 3C illustrates the prostate cancer-specific overall survival for the good and poor outcome groups in the SYS cases. SYS cases whose tumor classified as having a poor outcome had significantly increased hazard of suffering a prostate cancer-specific death (HR=2.3, 95% CI: 1.3-4.2). The median survival from first positive bone scan or CT was 3.1 years (95% CI: 2.5-4.3) in the group classified as having a poor outcome and 8.6 years (95% CI: 8.3-∞) in the group classified as having a good outcome (log rank p-value=0.0033).

Exploratory 8q24 Studies:

Because of recent tumor chromosome dosage and germ line association studies, the custom array included 82 8q genes on the custom array. Fourteen 8q genes were within the top 68 genes upon univariate analysis (Table 2). Compared to the proportion of 8q gene on both arrays the prevalence of 8q genes is non random (p=0.003, Fisher exact test). Twelve additional 8q genes were within the top 126 genes. The prevalence of 26 8q genes in the top 126 is statistically significant (p=$1.56 \times 10^{-5}$, Fisher exact test). Chromosome band 8q24.1 has the greatest over-representation of genes in the top 68 gene and 126 gene lists (11 genes, p=$6.35 \times 10^{-7}$ and 19 genes, p=$9.34 \times 10^{-12}$, Fisher exact test). Of the 17 genes/probes in our final model, 5 map to 8q24 (p=0.0043, Fisher exact test)(see Table 3).

Figure 4:
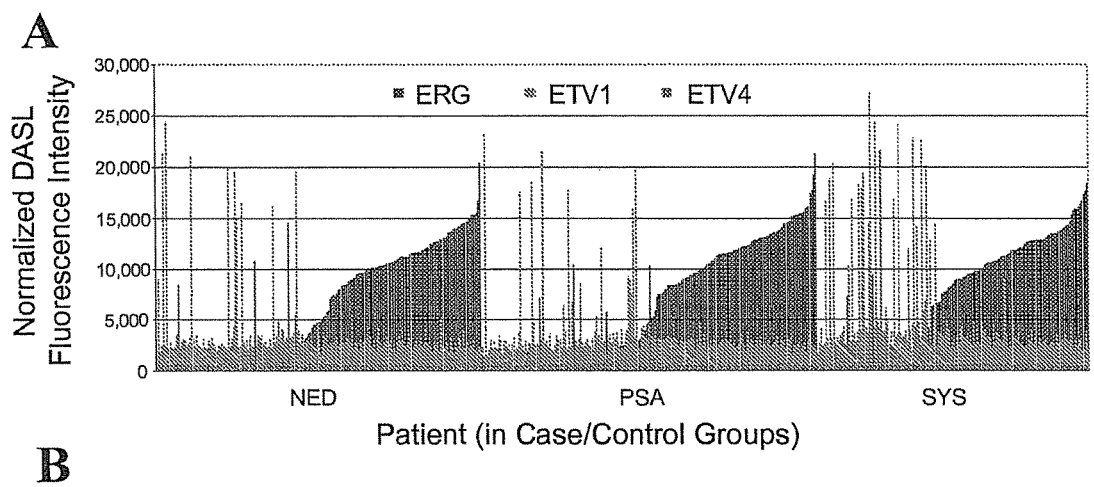
FIG. 4: Expression results for ERG, ETV1 and ETV4 among the men with no evidence of disease progression (NED), PSA recurrence (PSA) and systemic progression (SYS). (A) Each overlapping set of three bars represent a different a different case or control. Thresholds for overexpression are ERG>3200, ETV1>6000 and ETV4>1400. (B) The numbers of cases showing overexpression of one or more of ERG, ETV1 and ETV4 are shown.

Exploratory ETS Transcription Factor Studies:

Alterations of several ETS-family oncogenes are associated with the development of prostate cancer (Tomilins et al., Science. 310, 644-648 (2005); Tomlins et al., Cancer Res. 66, 3396-3400 (2006); and Demichelis et al., Oncogene. 26:4596-4599 (2007)). Oligonucleotide probe sets for the three major members of the ETS family involved in prostate cancer were included: ERG, ETV1, and ETV4, as well as their translocation partner TMPRSS2. FIG. 4 summarizes the expression results for these genes for the SYS cases and the PSA and NED controls. Several observations can be made: 1) With only 8 exceptions ERG, ETV1 and ETV4 overexpression are mutually exclusive; e.g. the overexpression of each generally occurs in different tumors. 2) Different probe sets for ERG give nearly identical expression results (FIG. 8A). 3) The prevalence of ERG overexpression was 50.0%, 52.2% and 53.8% in the SYS cases, PSA controls and NED controls, respectively (using a cutoff of 3200 normalized fluorescence units—see FIG. 4). There is no significant difference in the mean expression and the prevalence of ERG overexpression between the three cohorts. 4) The prevalence of ETV1 overexpression was 11.5%, 6.5% and 5.1% in the SYS cases, PSA controls and NED controls, respectively (using the cutoff of 6000 normalized fluorescence units—see FIG. 4). The prevalence of ETV1 overexpression was significantly higher in SYS Cases (p=0.043, chi-square test). 5) The prevalence of ETV4 overexpression ranged from 2.5%-5.5% among the three groups and was not significantly different. 6) None of the genes were selected by the formal statistical modeling (see Table 3). In fact, the 17 gene/probe model predicted similar rates of progression in ERG+ and ERG− patients.

Exploratory Pathway Analysis:

The 461 genes from both cancer and custom panels that are potentially differentially expressed between SYS cases and PSA controls (p<0.05) were used as the focus genes for Ingenuity Pathway Analysis (IPA, Ingenuity Systems Inc., Redwood City, Calif.). IPA identified 101 canonical pathways that are associated with the focus genes, 51 of which are over-represented with p<0.05 (see Supplemental Table 5 of U.S. Provisional Patent Application No. 61/057,698, filed May 30, 2008). However, because a limited number of genes on both DASL panels was measured, the p values from IPA analysis may not accurately quantify the degree of over-representation of focus genes in each pathway.

Gene Set Enrichment Analysis (GSEA) (Subramanian et al., Proc Natl Acad Sci USA. 102, 15545-15550 (2005)) was then performed on chromosome 8 genes grouped by map location. Genes mapped to 8q24.1 had a significant p value (p=0.0002) with a FDR q value=0.001 (see Supplemental Table 6 of U.S. Provisional Patent Application No. 61/057,698, filed May 30, 2008).

It was concluded that the measurement of gene expression patterns may be useful for determining which men may benefit from additional therapy after PSA recurrence. These measurements should be included in prospective evaluation of various therapeutic interventions in this setting.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating prostate cancer in combination with predicting whether or not a human will later develop systemic disease associated with the prostate cancer, wherein said method comprises:
   (a) obtaining a RAD21, CDKN35, CCNB15, SEC14L15, BUB1, ALAS1, KIA0196, TAF2, SFRP4, STIP1, CTHRC1, SLC44A1, IGFBP3, EDG7, FAM94B, C8orf53, and CDK10 nucleic acid expression profile for cancer tissue obtained at the time of PSA reoccurrence or retropubic radical prostatectomy from said human,
   (b) prognosing said human as later developing systemic disease based on at least said expression profile, and
   (c) providing early androgen ablation to said human prognosed as later developing systemic disease based on at least said expression profile.

2. The method of claim 1, wherein said method is performed at the time of said PSA reoccurrence.

3. The method of claim 1, wherein said method is performed at the time of said retropubic radical prostatectomy.

4. The method of claim 1, wherein said prognosing step (b) comprises prognosing said human as later developing systemic disease based on at least said expression profile and a clinical variable.

5. The method of claim 4, wherein said clinical variable is selected from the group consisting of a Gleason score and a revised Gleason score.

6. The method of claim 4, wherein said clinical variable is selected from the group consisting of a Gleason score, a revised Gleason score, age at surgery, initial PSA at recurrence, use of hormone or radiation therapy after radical retropubic prostatectomy, age at PSA recurrence, the second PSA level at time of PSA recurrence, and PSA slope.

7. A method for treating prostate cancer and predicting whether or not a human, at the time of systemic disease, will later die from the prostate cancer, wherein said method comprises:
   (a) obtaining a RAD21, CDKN35, CCNB15, SEC14L15, BUB1, ALAS1, KIA0196, TAF2, SFRP4, STIP1, CTHRC1, SLC44A1, IGFBP3, EDG7, FAM94B, C8orf53, and CDK10 nucleic acid expression profile for cancer tissue obtained at the time of PSA reoccurrence or retropubic radical prostatectomy from said human,
   (b) prognosing said human as later dying of said prostate cancer based on at least said expression profile, and
   (c) providing early androgen ablation to said human prognosed as later dying of said prostate cancer based on at least said expression profile.

8. The method of claim 7, wherein said prognosing step (b) comprises prognosing said human as later dying of prostate cancer based on at least said expression profile and a clinical variable.

9. The method of claim 8, wherein said clinical variable is selected from the group consisting of a Gleason score and a revised Gleason score.

10. The method of claim 8, wherein said clinical variable is selected from the group consisting of a Gleason score, a revised Gleason score, age at surgery, initial PSA at recurrence, use of hormone or radiation therapy after radical retropubic prostatectomy, age at PSA recurrence, the second PSA level at time of PSA recurrence, and PSA slope.

11. A method for treating prostate cancer, comprising: (1) predicting whether or not a human patient, at the time of PSA reoccurrence, will later develop systemic disease, (2) predicting whether or not a human patient, at the time of retropubic radial radical prostatectomy, will later develop systemic disease, or (3) predicting whether or not a human patient, at the time of systemic disease, will later die from prostate cancer, wherein said method comprises obtaining a RAD21, CDKN3, CCNB1, SEC14L1, BUB1, ALAS1, KIAA0196, TAF2, SFRP4, STIP1, CTHRC1, SLC44A1, IGFBP3, EDG7, FAM49B, C8Orf53, and CDK10 nucleic acid expression profile for cancer tissue from the human patient, determining that the expression profile is indicative of a later development of said systemic disease or said death, and providing early androgen ablation to said human patient.

* * * * *